(12) United States Patent
Creighton

(10) Patent No.: US 11,957,848 B2
(45) Date of Patent: Apr. 16, 2024

(54) MAGNETICALLY CONTROLLED MEDICAL DEVICES FOR INTERVENTIONAL MEDICAL PROCEDURES AND METHODS OF MAKING AND CONTROLLING THE SAME

(71) Applicant: UNandUP, LLC., Saint Louis, MO (US)

(72) Inventor: Francis M. Creighton, St. Louis, MO (US)

(73) Assignee: UNandUP, LLC, St. Louis, MO (US)

( * ) Notice: Subject to any disclaimer, the term of this patent is extended or adjusted under 35 U.S.C. 154(b) by 537 days.

(21) Appl. No.: 16/851,699

(22) Filed: Apr. 17, 2020

(65) Prior Publication Data

US 2020/0330730 A1 Oct. 22, 2020

Related U.S. Application Data

(60) Provisional application No. 62/868,972, filed on Jun. 30, 2019, provisional application No. 62/835,695, filed on Apr. 18, 2019.

(51) Int. Cl.
| | |
|---|---|
| *A61M 25/00* | (2006.01) |
| *A61L 2/00* | (2006.01) |
| *A61M 25/01* | (2006.01) |
| *A61M 25/09* | (2006.01) |

(52) U.S. Cl.
CPC ........... *A61M 25/0158* (2013.01); *A61L 2/00* (2013.01); *A61M 25/0009* (2013.01); *A61M 25/0127* (2013.01); *A61M 25/09* (2013.01); *A61L 2202/24* (2013.01); *A61M 2025/0166* (2013.01);

(Continued)

(58) Field of Classification Search
CPC .......... A61M 25/0127; A61M 25/0158; A61M 2025/0166
See application file for complete search history.

(56) References Cited

U.S. PATENT DOCUMENTS

| | | | |
|---|---|---|---|
| 4,005,699 A | * | 2/1977 | Bucalo .................... A61F 2/26 604/82 |
| 5,931,818 A | | 8/1999 | Werp et al. |
| 6,292,678 B1 | | 9/2001 | Hall et al. |

(Continued)

FOREIGN PATENT DOCUMENTS

| | | | |
|---|---|---|---|
| JP | 2013000222 A | * 1/2013 | |
| WO | WO-0193939 A1 | * 12/2001 | ........ A61M 25/0127 |

*Primary Examiner* — William R Carpenter
(74) *Attorney, Agent, or Firm* — Polsinelli PC

(57) ABSTRACT

A method of making magnetically controllable devices for interventional medical procedures comprises the steps of: Manufacturing a medical device for interventional medical procedures having magnetic materials which are without permanent magnetization; and establishing permanent magnetization within the magnetic materials subsequent to manufacturing, wherein the permanent magnetization allows the medical device to be magnetically controllable. The method may further including the step of packaging and sterilizing the medical device, wherein establishing permanent magnetization occurs after packaging and sterilization. The establishing permanent magnetization within the magnetic materials may include providing different magnetic orientations to distinct portions of the magnetic materials. The magnetic material includes one of a platinum alloy or a palladium alloy.

9 Claims, 18 Drawing Sheets

(52) U.S. Cl.
CPC . *A61M 2205/0272* (2013.01); *A61M 2207/10* (2013.01)

(56) References Cited

U.S. PATENT DOCUMENTS

| | | | |
|---|---|---|---|
| 6,375,606 B1 * | 4/2002 | Garibaldi | A61L 24/001 600/12 |
| 6,817,364 B2 | 11/2004 | Garibaldi et al. | |
| 7,066,924 B1 | 6/2006 | Garibaldi et al. | |
| 7,603,905 B2 | 10/2009 | Creighton, IV | |
| 7,757,694 B2 | 7/2010 | Ritter et al. | |
| 7,771,415 B2 | 8/2010 | Ritter et al. | |
| 7,974,678 B2 | 7/2011 | Maschke | |
| 8,092,450 B2 | 1/2012 | Davies et al. | |
| 8,419,681 B2 | 4/2013 | Sell | |
| 2002/0072758 A1 * | 6/2002 | Reo | H01F 41/026 606/153 |
| 2006/0079812 A1 | 4/2006 | Viswanathan | |
| 2007/0016131 A1 * | 1/2007 | Munger | A61M 25/09 604/95.01 |

* cited by examiner

MAGNETICALLY CONTROLLED MEDICAL DEVICES FOR INTERVENTIONAL MEDICAL PROCEDURES AND METHODS OF MAKING AND CONTROLLING THE SAME

RELATED APPLICATIONS

This application claims priority to U.S. Provisional Patent Application Ser. No. 62/835,695, filed Apr. 18, 2019 titled "Magnetically Controlled Linkage Based Devices" which is incorporated herein by reference. This application claims priority to U.S. Provisional Patent Application Ser. No. 62/868,972, filed Jun. 30, 2019 titled "Novel Magnetically-Controlled Programmable Magnetic Devices" which is incorporated herein by reference.

BACKGROUND INFORMATION

1. Field of the Invention

The present invention relates to magnetically controllable medical devices for interventional medical procedures, and methods of making and controlling the same.

2. Background Information

The use of magnetic fields in medicine is not new. In 1873, Dr. Julius Hirschberg is often credited with being the first to use an electromagnet to remove iron filings from the eye. From that time onward, magnetism in medicine quickly expanded, including uses of iron compounds to deliver hyperthermia for tumors in 1957, thrombosis inducement within aneurysm sacks in 1965, embolization of tumors in 1973, and to enhanced imaging for MR procedures in 1982, to name a few milestones. The present invention is directed to the field of controlling medical devices in interventional medical procedures, which conventionally are manually controlled, or now sometimes robotically controlled. Within the meaning of the present invention the phrase "interventional medical procedure" refers to medical procedures conducted within a body lumen, a body cavity and/or a body chamber. Further, medical devices for interventional medical procedures are devices constructed for performing medical procedures and treatments within a body lumen, a body cavity and/or a body chamber.

Manually-controllable medical devices for interventional medical procedures, e.g., guidewires, coils, lumens, microcatheters, catheters, sheaths, can be difficult to navigate within small and tortuous vasculature. As a result, their use can lead to long procedure times, expose operators and patients to increased ionizing radiation, and contribute to poor clinical patient outcomes.

Manually navigating traditional guidewires is a complex procedure. Generally, operator-induced manual forces and torques are inefficiently transmitted from the medical device's proximal end, which is located outside the patient, to the device's distal end, which is often over a meter away, wherein tension often can build along the device's length so that control over the device's distal end is problematic. For this reason, guidewire navigation is often limited to navigating guidewires with diameters of about 0.014 in (or more) within vessels generally larger than a few millimeters in diameter, and which vessels are not tortuous in nature. These factors also limits the deployment of medical devices passed over the guidewire, such as stents, thrombectomy systems, aneurysm-filling coils, aspiration devices, and drug-delivery catheters.

Manual manipulation to shape the guidewire's tip prior to insertion into the body can often be required. During a procedure, if the guidewire's tip angle is inadequate, the guidewire must be removed from the body and the tip manipulated and then redeployed.

While robotic platforms have addressed deficiencies associated with manual navigation of catheters in and around the heart, no commercial solutions currently exist to robotically navigate guidewires in the body. The main reasons for this include the cost, size, and increased complexity of the robotic technologies.

One illustrative example relating to the present invention includes performing a mechanical thrombectomy (generally referenced as simply a thrombectomy) within the neurovasculature in the event of acute ischemic stroke (AIS). AIS is the result of a blood clot in a cerebral artery. Each year, AIS impacts nearly 700,000 Americans. It is the leading cause of long-term disability and the fifth-leading cause of death in the US. While US annual costs associated with AIS are already high, they are projected to further increase to $183 billion by 2030. Brain tissue rapidly dies when deprived of blood, thus the time to reperfusion is critical in preventing death and improving neurological outcomes. AIS victims have few treatment options. Intravenous thrombolysis remains the standard of care for AIS; however, earliest-possible thrombectomy has been proven effective and is now recommended for proximal large vessel occlusions in the anterior circulation, which account for up to half of all annual AIS events. In 2015, the results of five trials from different countries were published in the New England Journal of Medicine, demonstrating the safety and efficacy of mechanical thrombectomy with stent-retrievers in improving outcomes and reducing mortality for patients who present within 6 hours from their time last known well. It is now a widespread procedure performed in most primary, thrombectomy capable, or comprehensive stroke centers across the globe. In 2018 the DAWN and DEFUSE-3 trails were published. These trials showed that mechanical thrombectomy is a safe and effective treatment for individuals who have an acute ischemic stroke out to 24 hours of symptom onset.

Transfer-related delays are a known dilemma, which range between 40 minutes and 120 minutes, of the many factors that drive neurological outcomes. Currently, more than half of Americans face transfer times longer than 60 minutes, where the delay between stroke onset and thrombectomy averages 4 hours. This barrier to early thrombectomy access partially explains why nearly half of all thrombectomy recipients die or left moderately-to-severely disabled, with only 10% showing a complete recovery.

In the US, thrombectomies are predominately performed at centers certified as Comprehensive Stroke Centers (CSCs) by the Joint Commission on Accreditation of Healthcare Organizations (JCAHO), for which there are about 170 as of the year 2019. CSC certification is associated with the extensive requirements, including access to high-level expertise, 24/7 access to care, dedicated neuro intensive care beds, on-site thrombectomy, CT/MR/CTA/MRA imaging, and participation in clinical research. The considerable costs associated with setting up and maintaining a CSC result in these centers tending to be concentrated near highly-populated urban centers, which can provide higher patient volumes. Consequently, rural and suburban US citizens face substantial transfer delays which can exceed 2 hrs.

To equalize thrombectomy access in the US, the JCAHO, in collaboration with the American Heart and American Stroke associations, announced the Thrombectomy-Capable Stroke Center (TSC) certification program on Jan. 1, 2018. While this program strives to build a geographically-dispersed thrombectomy-capable hospital network, concerns remain regarding the expense of providing 24/7 care, recruiting from the pool of less than 3500 neuroradiologists, and procuring the highest-level of expertise. As a result, there is an ongoing debate as to whether interventional cardiologists, of which there are nearly five-thousand and whose myocardial infarction services are already geographically distributed and operate 24/7, might be trained to perform thrombectomy as associated with AIS. In general, neurointerventionalists feel that the advantage of improved access offered by emerging "neuro-cardiologists" cannot offset the experience of highly-skilled stroke interventionalists.

In general, guidewire navigation in the neurovascular is required to perform a range of procedures, which include, but are not limited to, thrombectomy, stenting, and repair of aneurysms. Because the guidewire is easier to navigate within the vasculature than bulker tools, the guidewire is usually navigated to the desired region prior to a tool being delivered over the guidewire. In this way, the guidewire enables easier access of otherwise inaccessible regions. However, successful guidewire navigation can represent a complex procedure. For example, thrombectomy requires a thorough understanding of AIS, treatment options, imaging data, and how to safely and effectively navigate small devices within tortuous vasculature. While some wire-navigation procedural aspects may be straightforward (e.g., navigation from the femoral artery to the aortic arch), other aspects can be difficult (e.g., navigating the aortic arch, stenotic internal carotid arteries (ICAs), and tortuous middle cerebral arteries (MCAs)). Because neurovascular guidewire devices are manipulated from over a meter away from the device's tip, force and torque errors can accumulate as the interventionists pushes, pulls, or rotates the guidewire. Often, the guidewire must be manually shaped, or removed from the patient and reshaped. Thus, navigation can be challenging unless the neuro-interventionist is active, skilled, and highly experienced.

The need to geographically expand early access to thrombectomy is hampered by inadequate access to AIS thrombectomy expertise, therefore the use of interventional robotics to improve access has been recognized as a way to bridge this divide. Robotic strategies have been used since 1985 to assist urological, gynecological, and electrophysiology procedures, however, these approaches have yet to offer value for neurovascular interventions (including for the purposes of a thrombectomy).

While, as of 2019, there are no approved robotic system for navigating guidewires in the body, the robotic platforms manufactured by Hansen Medical and Stereotaxis are closest in meeting some interventional neuroradiology needs. Both platforms are currently approved for electrophysiology (EP) treatment of cardiac arrhythmias. Having performed more than 100,000 cardiac ablation procedures, the magnet-based technology of Stereotaxis remains dominant. While both robotic technologies reduce x-ray exposure by placing the physician outside the x-ray field, broad adoption has been limited.

Hansen Medical's platform manipulates standard medical devices and remains hampered by force/torque transmission errors to the device's tip. Within EP, the technology has struggled to demonstrate better safety, device control, and ease-of-us. While Stereotaxis' robotic platform exerts better catheter control by using magnetic fields to deflect magnet-tipped catheters, the system is impractically large (3200 kg), hard to install, and difficult to use. Importantly, both technology platforms are very expensive (>$600,000 for the robotic platform from Hansen Medical, >$2,000,000 for the robotic platform from Stereotaxis). In terms of the ability of these robotic platforms to improve neuroradiology procedures, both have faced considerable hurdles. Hansen Medical's technology is hindered by inherent limitations of existing guidewires where pushing, pulling, and rotation of the guidewire from the proximal end can result in large errors at the guidewire's tip. In contrast, Stereotaxis' technology is able to effectively deliver magnet torques directly to their magnet-tipped guidewires; however, Stereotaxis abandoned its guidewire product due to incompatibilities with the neuro-angiography suite, which included the large magnet mass employed (800 kg), the inability to integrate with the neuro-angiography suite's larger c-arm-mounted digital plates, an excessive purchase price, and reduced patient access.

In conclusion, while the potential benefit of robotic technologies to expand early access to thrombectomy is high, prior robotic strategies have largely failed in meeting the complex needs of these procedures and workflows. While Stereotaxis' technology comes close to meeting these needs, the company ultimately abandoned magnetic guidewire navigation due to their technology's excessive size and cost, and incompatibilities with the neuro-angiographic imaging.

There remains a need for systems that provide remote guidance of interventional tools by highly-skilled neuro-interventionists regardless of their geographic location. In effect, comprehensive stroke centers (CSCs) would be able to greatly broaden their geographic reach. In addition, such a technology could prove valuable in assisting emerging neuro-cardiologists as they perform thrombectomy procedures. If successful, such a technology would ensure all AIS victims would have equal and rapid access to standard-of-care thrombectomy.

The patent literature describes systems analogous to the commercialized Stereotaxis' technology. See for example the magnetically navigable guidewire disclosed in Werp et al., U.S. Pat. No. 5,931,818 (owned by Stereotaxis and incorporated in its entirety herein by reference), wherein the user can advance the magnetically navigable guide wire into vessels with little or no contact between the end of the wire and the vessel wall. When the distal end of the guidewire is adjacent the vessel of interest, the user operates a magnetic system to apply a magnetic field, preferably with the aid of a computerized user interface, to deflect the wire tip to align with the vessel side branch. The deflection of the guidewire tip is controlled by the external magnets in magnetic navigation, and in normal use, the physician does not need to apply torque to the guidewire. See also U.S. Pat. No. 8,419,681 titled "Magnetically Navigable Balloon Catheters", U.S. Pat. No. 8,092,450 titled "Magnetically Guidable Energy Delivery Apparatus and Method of Using Same", U.S. Pat. No. 7,974,678 titled "Catheter for Magnetic Navigation", U.S. Pat. No. 7,771,415 titled "Method for Safely and Efficiently Navigating Magnetic Devices in the Body", U.S. Pat. No. 7,757,694 titled "Method for Safely and Efficiently Navigating Magnetic Devices in the Body", U.S. Pat. No. 7,603,905 titled "Magnetic Navigation and Imaging System", U.S. Pat. No. 7,066,924 titled "Method of and Apparatus for Navigating Magnetic Devices in Body Lumens by a Guide Wire with a Magnetic Tip", U.S. Pat. No. 6,817,364 titled "Magnetically Navigated Pacing Leads, and Methods for Delivering Medical Devices", U.S. Pat. No. 6,292,678 titled "Method of Magnetically Navigating Medical Devices with Magnetic Fields and Gradients, and Medical Devices Adapted Therefor", and U.S. Publication 2006-0079812 titled "Magnetic Guidewire for Lesion Crossing, which are incorporated herein by reference. However, generally the prior magnetically navigable systems discussed and proposed in the patent literature suffer from the same deficiencies as the commercialized Stereotaxis technology.

There remains a need in the art for cost effective, efficient magnetically controllable devices for interventional medical procedures.

SUMMARY OF THE INVENTION

One aspect of this invention is directed to magnetically controllable devices for interventional medical procedures. The phrase "magnetically controllable" relative to a medical device for interventional medical procedures is defined herein as wherein a known external magnetic field exerted on the device induces a force or torque on the device; causes a change in shape or orientation of the device; or induces a change or a temporal effect in a property of the medical device (such as heating or causing the device to vibrate). The magnetic field applied to the medical device may be a static magnetic field meaning it does not change over time, or a dynamic or temporal magnetic field that varies over time. Magnetically-induced forces and torques on the magnetically-controlled magnetic medical device for interventional medical procedures may be described as, but are not limited to the following: bending, twisting, deflecting, angulating, turning, aiming, angling, orienting, winding, and coiling. Magnetically-induced temporal effects on the magnetically-controlled magnetic medical device for interventional medical procedures may be described as, but are not limited to the following: vibrating, wiggling, agitating, oscillating, rotating, shaking, pulsating, disturbing, mixing, fluctuating, undulating, revolving, spinning, circling, gyrating, twirling, and turning.

One aspect of the present invention provides a method of making magnetically controllable devices for interventional medical procedures comprising the steps of: Manufacturing a medical device for interventional medical procedures having magnetic materials which are without permanent magnetization; and Establishing permanent magnetization within the magnetic materials subsequent to manufacturing, wherein the permanent magnetization allows the medical device to be magnetically controllable.

The method of making magnetically controllable devices for interventional medical procedures according to the present invention may further including the step of packaging the medical device for interventional medical procedures and wherein the step of establishing permanent magnetization occurs after packaging the medical device. The method of making magnetically controllable devices for interventional medical procedures according to the present invention may further including the step of sterilizing the medical device for interventional medical procedures and wherein the step of establishing permanent magnetization occurs after sterilizing the medical device.

The method of making magnetically controllable devices for interventional medical procedures according to the present invention may provide wherein the step of establishing permanent magnetization within the magnetic materials subsequent to manufacturing includes providing different magnetic orientations to distinct portions of the magnetic materials.

The method of making magnetically controllable devices for interventional medical procedures according to the present invention may provide wherein the magnetic material includes one of a platinum alloy or a palladium alloy. The method of making magnetically controllable devices for interventional medical procedures according to the present invention may provide wherein the magnetic material includes one of platinum cobalt (PtCo), platinum iron (PtFe), cobalt palladium (CoPd), nickel platinum (NiPt), nickel palladium (NiPd), and alloys containing iron, platinum, and niobium. The method of making magnetically controllable devices for interventional medical procedures according to the present invention may provide wherein the magnetic material includes platinum cobalt (PtCo) formed of wires less than 1 mm in diameter.

The method of making magnetically controllable devices for interventional medical procedures according to the present invention may provide wherein the medical device is one of a guidewire or a catheter, specifically wherein the medical device is one of a guidewire having an outer diameter less than 0.035 in, preferably less than or equal to 0.014 in, or a catheter with an outer diameter less than 2 mm and an inner diameter less than 1.5 mm.

Another aspect of the present invention provides a magnetically controllable medical device for interventional medical procedures having magnetic materials in which has been established permanent magnetization, wherein the permanent magnetization allows the medical device to be magnetically controllable, and wherein the magnetic material includes one of a platinum alloy or a palladium alloy. The magnetically controllable medical device for interventional medical procedures according to the invention may provide wherein the magnetic material includes one of platinum cobalt (PtCo), platinum iron (PtFe), cobalt palladium (CoPd), nickel platinum (NiPt), nickel palladium (NiPd), and alloys containing iron, platinum, and niobium.

Another aspect according to the present invention provides a magnetically controllable medical device for interventional medical procedures having magnetic materials in which has been established permanent magnetization, wherein the permanent magnetization allows the medical device to be magnetically controllable, and wherein the medical device is one of a guidewire having an outer diameter less than 0.035 in or a catheter with an outer diameter less than 2 mm.

The features that characterize the present invention are pointed out with particularity in the claims which are part of this disclosure. These and other features of the invention, its operating advantages and the specific objects obtained by its use will be more fully understood from the following detailed description in connection with the attached figures.

DETAILED DESCRIPTION OF THE PREFERRED EMBODIMENTS

Figure 1:
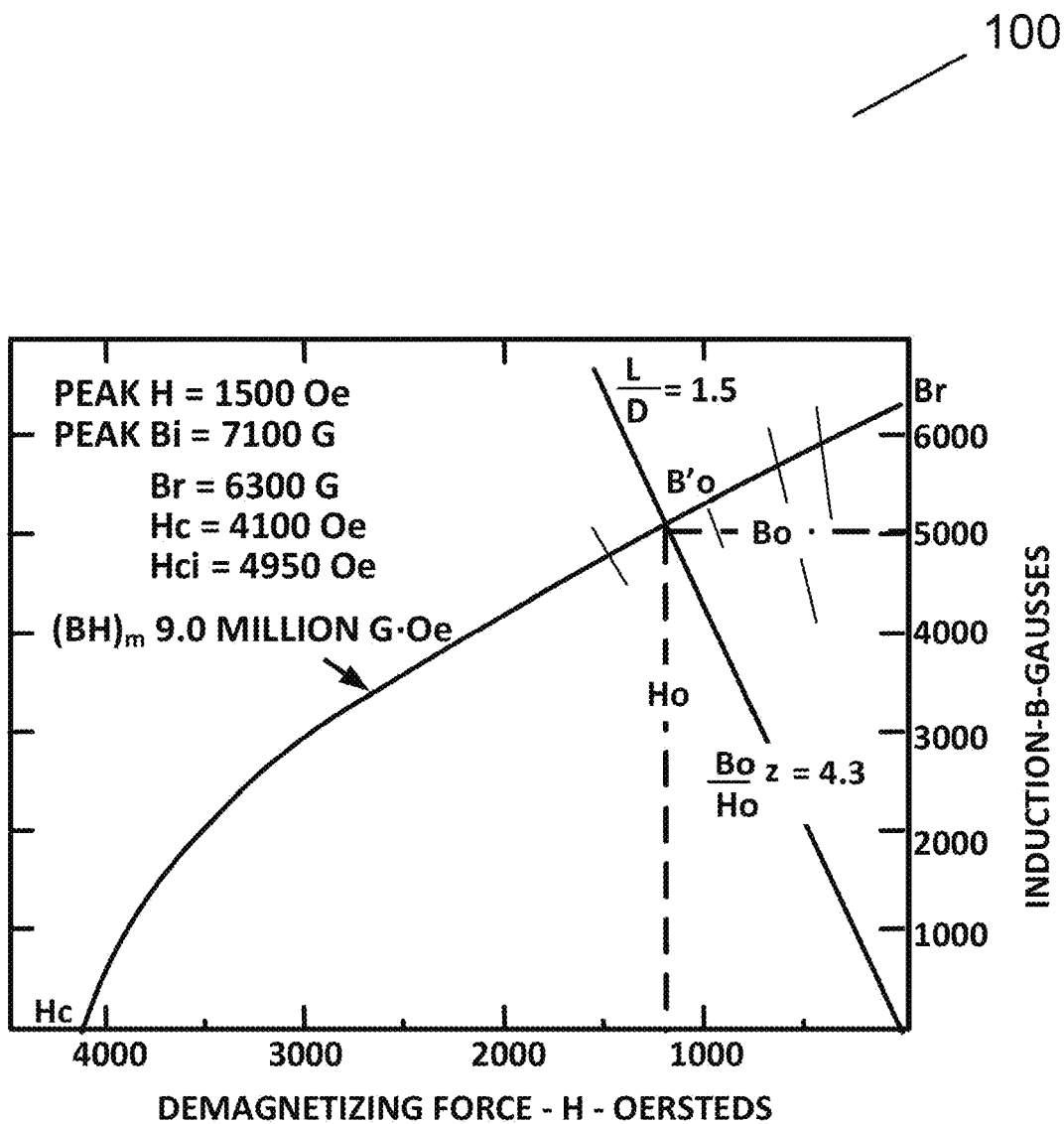
FIG. 1 is a drawing of a demagnetization curve for a platinum cobalt alloy.

The present invention relates to cost effective, efficient magnetically controllable medical devices for interventional medical procedures. As discussed above the meaning of the present invention the phrase "interventional medical procedure" refers to medical procedures conducted within a body lumen, a body cavity and/or a body chamber. Further, medical devices for interventional medical procedures are devices constructed for performing medical procedures and treatments within a body lumen, a body cavity and/or a body chamber. Finally, the phrase "magnetically controllable" relative to a medical device for interventional medical procedures is defined herein as wherein a known external magnetic field exerted on the medical device induces a force or torque on the device; causes a change in shape or orientation of the device; or induces a change or a temporal effect in a property of the medical device.

The proposed inventions described in detail below overcome prior limitations which have prevented the use of robotics to effectively navigate guidewires in the body. In accordance with the principles of the present invention, by leveraging a unique ductile magnetic alloy whose magnetization can be established or programmed post manufacturing, small magnetically-controllable medical devices can be made which can be magnetically-controlled using a compact external magnetic-field generating system composed of an array of one or more magnets. Because forces and torques are magnetically and directly induced on the magnetically-controlled programmable magnetic medical device's tip, the inefficiency of transmitting manually-generated forces and torques from the device's proximal end is overcome. As a result, smaller interventional devices can be built and effectively navigated, such as interventional guidewires and catheters. As detailed below the magnetically controlled medical devices for interventional medical procedures may be considered as programmable magnetic materials because the orientations(s) and magnitudes of the permanent magnet material can be established according to the design specifications post manufacturing.

One innovation described herein is the use of a platinum cobalt (PtCo) alloy to navigate small interventional devices using a magnet system smaller than previously possible. PtCo permanent magnets were discovered in the 1930's and heavily researched until the late 1960's when magnetically-stronger samarium-cobalt (SmCo) sintered magnets were introduced, which in turn have now been largely replaced by neodymium-boron-iron (NdBFe) magnets. Research found that the ideal PtCo permanent-magnet alloy was Pt-23 wt % Co, which yielded an energy product of ~9 MGOe. While weaker than modern permanent magnets, PtCo is a ductile and flexible material which retains its form post shaping and can be drawn into fine, small 0.1 mm outer-diameter (OD) wires, a capability not possessed by sintered magnets. Once PtCo is shaped, annealing locks the magnetic phase so that magnetization is retained. PtCo is a particularly useful medical device material in that it is chemically inert, resistant to acids and bases, and is x-ray opaque (~75 wt % platinum). Magnetically, PtCo can be formed into complex submillimeter shapes without a loss in magnetization. Thus, it is straightforward to create magnetic guidewires by replacing the standard (nonmagnetic) platinum coil with one composed of PtCo.

In contrast with the PtCo magnetic material, SmCo and NdBFe sintered magnets suffer substantial surface demagnetizations from grinding and/or electrical discharge machining. Also, the orientation of the preferred magnetization axis is hard to maintain and structures smaller than 1 mm easily fracture when magnetized.

Another innovation described below is that PtCo materials can be used to navigate micro-catheters where the catheter's tip and/or braid is composed of loops, coils, or patterns of PtCo material which do not impinge upon the lumen. This offers the possibility of enabling new therapies for distal clots, which include, but are not limited to, passing clot retrieving device, aspiration, and drug delivery. Distal emboli are known to result from thrombectomy procedures and have been observed in up to half of cases. Despite known to adversely affect neurological outcomes, these emboli are largely left untreated due to the smallness of the vessels and the risk of aggravating ischemic injury. Magnetically-guidable PtCo micro-catheters according to the present invention offers novel strategies and tools to remove these otherwise untreatable emboli, including intra-arterially-directed thrombolytics, vacuum aspiration, and clot retrieval.

Additionally, because the magnetic requirements are greatly reduced, novel magnet designs and controlling methods are possible that are optimized for the neuro-angiography suite. For example, a 20 kg magnet (vs. 800 kg of magnet material for the Stereotaxis Niobe system) provides clinically-relevant PtCo guidewire deflections. Because of the magnet's substantial size reduction, the system can be integrated into neuroradiology workflows and moved to avoid obstructing x-ray imaging. A known benefit of magnet-based navigation is that precise forces and torques can be applied directly to magnet-tipped devices, which eliminates the need to bend the tip or to rotate the guidewire from the proximal end. One unique aspect of the proposed technology is the ability to provide closed-loop guidewire navigation where the user's input, CT map, real-time imaging, device advancer, and the external magnet operate together to safely drive the device to the intended target.

It is instructive to consider a simplified model for the guidewire's restoring torque: $\tau_r = \lambda\theta/L$, where $\tau_r$, $\lambda$, $\theta$, and $L$ denote the torque, restoring proportionally constant, tip deflection angle, and guidewire's deflection length, respectively. In equilibrium, the magnetic torque, $\tau_B$, balances the restoring torque so that $\tau_B = mB \sin(\beta-\theta) = \lambda\theta/L$, where m, B, and $\beta$ are the tip's magnetic moment, the magnetic field strength, and the deflection angle of the magnetic field (which leads $\theta$). Thus, the desired deflection angle requires the optimal solution for $\beta$ and B which must be calculated quickly and result in repositioning of the external magnet with minimal lag. The software and robotic methods associated with this process are considered novel and offer the opportunity to implement machine learning in the future.

It is helpful in understanding the present invention to note that magnetic resonance imaging (MRI), for which a uniform magnetic field is generated, is not able to control the magnetically-controlled programmable magnetic medical devices for interventional procedures described in this invention. The uniformity of the MRI's magnetic field results in a near-zero magnetic spatial gradient within the MRI's bore. While the tip of the magnetically-controlled programmable magnetic device will orient to align with the MRI's magnetic field direction, desired radial deflections cannot be specified because of cylindrical symmetry of the magnetic fields (i.e., magnetic deflections away from the axis can go in any direction with no preference with respect to the angle around the axis). Furthermore, while the MRI's gradient coils are designed to encode space so that imaging is possible, the generated gradient is weak in terms of its magnetic magnitude and the gradient pulse is generated for a very short time (e.g., less than a second). As a result, the MRI's gradient coils cannot be used to effectively control the magnetically-controlled programmable magnetic medical devices proposed herein.

One of the unique aspects of PtCo magnetic materials is that permanent magnetization can be established post manufacturing of the PtCo-composed component. This is in contrast to sintered permanent magnets (e.g., NdBFe and SmCo) whose preferred axis of magnetization must be established prior to sintering. As a result, knowledge of the sintered magnet's preferred magnetization direction must be accounted for during magnet grinding, cutting, and shaping, which can be highly difficult to maintain. Although sintered magnets are magnetically stronger, small-scale machining of sintered magnets suffers from demagnetization and frequent fracturing which limits the achievable diameters to about 0.5 mm and larger. In contrast PtCo material is ductile and can be shaped into very small using standard approaches without a loss in their mechanical and magnetic characteristics.

In contrast to other magnet types, it is possible to establish or program preferred magnetizations of PtCo-composed devices post manufacturing of those devices so that better control is possible using an external magnet source. The external magnet source may consist of one or more external permanent and/or conducting magnets which compose a "magnet array". In establishing the preferred magnetization orientations along the magnetically-controlled "programmable magnet" device, a magnetizer can be used to program the magnetizations of the PtCo-composed devices, which must generate about one Tesla (~1 T). Magnetizers may consist of an array of one or more magnetic field-generating magnet sources.

One way to magnetize the PtCo-composed devices is to use an external magnet array to magnetize the entire device at once. In some cases, it may be useful to orient and fix the device in a specific orientation relative to the magnetizer's magnet array so that favorable magnetization orientations of the magnetically-controlled programmable magnet device align with the intrinsic magnetic field directions of the magnetizing magnet array.

In other cases, it may be useful to use a magnet array to magnetize individual segments of the device. The benefit of this strategy is the ability to impose greater magnetization orientation differences along the magnetically-controlled programmable magnetic device.

It is also possible to use an array of magnetizing magnets to create the desired magnetization angles and strengths along the magnetically-controlled programmable magnetic device.

It is also possible to use the external magnet array (also referred to as the magnet-based system or workstation), which is used to manipulate the magnetically-controlled programmable magnetic device, to induce the desired magnetization orientations and strengths along the magnetically-controlled programmable magnetic device.

Preferred magnetization of magnetically-controlled programmable magnetic devices can be performed during final packaging or performed prior to use using a magnetizer possessing a magnet array of one or more magnetizing magnets. Because magnetization can be accomplished without physically contacting the magnetically-controlled programmable magnetic device, the magnetically-controlled programmable magnetic device can remain inside its packaging during magnetization. For example, sterility would not be compromised for prepackaged magnetically-controlled programmable magnetic devices during magnetization. In addition, because some sterilization techniques employ high temperatures which can degrade magnetizations, magnetically-controlled programmable magnetic devices can be magnetized post sterilization without negatively affecting final performance of the magnetically-controlled programmable magnetic devices.

Another benefit of magnetizations being performed shortly before use is that best performance of the magnetically-controlled programmable magnetic device is preserved in that it is theoretically possible that the magnetically-controlled programmable magnetic device's magnetization could degrade over time and during shipment.

A benefit of different magnetization orientations along the magnetically-controlled programmable magnetic device is that certain magnetizations result in better control using the external magnet array. For example, it is possible to magnetize the magnetically-controlled programmable magnetic device so that torque is maximized at the maximum deflection using a mostly-uniform externally-generated magnetic field. Likewise, magnetizations of the magnetically-controlled programmable magnetic device can be programmed so that the deflection torque is maximized for non-uniform magnetic fields.

For other applications, the magnetizations along the magnetically-controlled programmable magnetic device can be programmed so that vibrations of the magnetically-controlled programmable magnetic device is possible using a time-changing external magnetic field. Vibration, or "wiggling", allows the magnetically-controlled programmable magnetic device to release tension and to overcome regions experiencing greater static friction, thereby enabling better control of the magnetically-controlled programmable magnetic device. An analogous device is a "snake" used to navigate the pipes of a home's plumbing system, where mechanical rotation of the snake allows the probe to advance further and easier. In contrast to the technology proposed herein, magnetic forces and torques are generated only on the magnetic components of the magnetically-controlled programmable magnetic device. Thus, ineffective transmission of mechanical forces from the proximal end of the magnetically-controlled programmable magnetic device are not required to induce vibrational motion.

The magnetically-controlled programmable magnetic devices may make use of other materials to improve behavioral performance. Permanent magnets (e.g., NdBFe, SmCo), other magnetic platinum alloys [e.g., platinum iron (PtFe)], and high-saturation magnetization permeable magnetic materials (e.g., high-purity iron) maybe incorporated with the magnetically-controlled programmable magnetic devices. As an example, the magnetically-controlled programmable magnetic device tip may make use of a gold-plated or gold-capped NdBFe magnet to improve the extent of magnetic deflection, where gold is used as a biocompatible surface.

The magnetically-controlled programmable magnetic devices may make use of other materials to improve visibility under x-ray imaging. These include, but are not limited to, other platinum alloys, gold, and radiopaque polymers.

The magnetically-controlled programmable magnetic devices proposed herein can provide navigational advantages for a range of conditions. These include, but are not limited to, faster navigation to the desired region, better navigation of tortuous or difficult vascular geometries, improved access of smaller vessels, better control within small volumes, and beneficial use in small regions. For example, current guidewires are manipulated from more than a meter away from the device's proximal end. As a result, the wires must be sufficiently large and stiff to transmit user-applied forces and torques from the device's proximal end. In contrast, the ability to apply magnetic forces and torques directly to the magnetically-controlled programmable magnetic device's tip removes the need for stiffness between proximal and distal ends of the device, thereby enabling interventional devices to be manufactured considerably smaller. This enables the novel guidewire to navigate smaller and more tortuous vessels.

As the magnetically-controlled programmable magnetic devices proposed herein can be navigated faster and better compared to other devices, other therapies and diagnostic modalities can be better provided. These include, but are not limited to, thrombectomy, stent placement, electrical lead placement, radiofrequency ablation, cryocooling ablation, laser ablation, microwave ablation, thermal ablation, cardiac ablation for arrythmias, tumor ablation, tissue biopsy, fluid sampling, navigation of tortuous vasculature (including the aortic arch), navigation of lumens within the body, embolization of tumors and vascular malformations, simulation of tissue, recordings of tissue electrical signaling, drug delivery, implantation of cells, localized delivery of gene-therapy modalities, force measurements of tissue, navigation of brain parenchyma or cerebral spinal fluid, bronchial tube and esophagus access, navigation within the stomach, colon, or intestines, navigation within the kidney or urethra, navigation of the inner ear, Eustachian tubes, sinus and nasal passages, or vessels or vitreous of the eye, navigation within the spinal column, and other laparoscopic interventions.

The favorable magnetic and mechanical properties of platinum cobalt (PtCo) also apply to other platinum or palladium based magnetic alloys, which include, but are not limited to, platinum iron (PtFe), cobalt palladium (CoPd), nickel platinum (NiPt), nickel palladium (NiPd), and alloys containing iron, platinum, and niobium.

Magnetically-controlled programmable magnetic devices according to the invention include, but are not limited to, wires, guidewires, catheters, radio-frequency wires, micro-catheters, caps, bands, braids, coils, lumens, thrombectomy systems, stents, aspiration tools, drug-delivery tools, aneurysm-filling coils, electrical leads, and embolization systems. The magnetically-controlled wires according to the invention may be described as, but is not limited to, guidewires, lines, leads, probes, or guides. The magnetically-controlled lumens according to the invention may be described as, but is not limited to, catheters, micro-catheters, sheaths, tubes, pipes, conduits, and hoses.

The magnetically-controlled wires and lumens of the invention may be composed of a range of materials which improve performance. Construction materials include, but are not limited to, permanent magnets, permeable magnets, biocompatible materials, plastics, stainless steel, metal, gold, brass, copper, titanium and/or titanium allows (e.g., nickel titanium), platinum and/or platinum allows (e.g., platinum cobalt and platinum iron), polymers, polyimides, silicone, nylon, polyurethane, polyethylene terephthalate, latex, thermoplastic elastomers, biocompatible materials, hydrophobic or hydrophilic materials, or ceramics materials.

To prevent bodily fluids from entering the devices of the invention, the magnetically controlled programmable magnetic devices can incorporate biocompatible covers and/or coatings. Example biocompatible fluid barriers make use of, but are not limited to, polymer, plastic, rubber, silicon, polyurethane, polytetrafluoroethylene (PTFE), and expanded PTFE.

The open lumen possible for some magnetically controlled programmable magnetic devices allows the passage of a number of therapeutically useful materials and/or modalities, including, but not limited to, electrically-conducting wires, irrigation, optical components, radiofrequency components, guidewires, micro-catheters, catheters, drugs, stem cells, embolization beads or glues, stimulators, biopsy tools, delivery tools and needles for drugs (including genes and stem cells), force sensors, ultrasound components, cryo-cooling, localization sensors, fiber optic cables, aspiration devices and mechanisms, brachytherapy tools, tissue and fluid sampling tools, imaging devices, tissue and bone fusion tools, thrombectomy, stents, and surgical intervention modalities and devices.

Manipulation of the magnetically controlled programmable magnetic devices may be described as, but is not limited to, the following: bending, deflecting, and orienting, configuring, angulating, articulating, rotating, positioning, repositioning, torqueing, swinging, and shifting. A controller may be used to control the magnetically controlled programmable magnetic devices where manipulations include, but are not limited to, advancement, retraction, rotation, tensioning, vibrating, and angulating.

The external magnet system for controlling the magnetically controlled programmable magnetic devices may be built from materials which generate a strong magnetic field. The external magnet system will be capable of generating the necessary magnetic field for controlling the magnetically controlled programmable magnetic devices. Magnets contained within the external magnet system may be composed from permanent magnetic materials, conducting magnets, or superconducting magnets. Articulation of the magnet may be used to ensure the required magnetic fields are generated on the magnetically controlled programmable magnetic devices. Articulation may include one or more rotation components and one or more translational components. Actuation of the rotational and/or translational components may be performed with a beneficial temporal profile. For example, a temporally-changing magnetic field may be employed which induces a vibration of the magnetically-controlled programmable magnet device. By doing so, tension can be released, and static friction can be overcome so that greater control of the magnetically-controlled programmable magnetic device is possible. In other scenarios, it may be useful to use more than one magnet system, whose magnetic fields can be made to combine so as to improve overall control of the magnetically controlled programmable magnetic devices.

The external magnet system may make use of magnetic shielding which alters the extension of the magnetic field within the environment the external magnet system is placed. For example, magnetic shielding may be used near magnetically-sensitive implants, equipment, or tools. For magnet systems composed of permanent magnetic materials (which cannot be deactivated as is the case with conducting or superconducting magnets), shielding may be use when the magnet is stowed. This serves the purpose of effectively deactivating the magnet system when not in use or during transportation.

The present invention can be better understood in connection with the attached figures which show distinct guidewire and catheter implementations of the concepts of the present invention. FIG. 1 is a schematic drawing of a demagnetization curve 100 for a platinum cobalt alloy (Pt-23% wtCo). As is noted, a length over diameter (L/D) ratio of 1.5 results in a material remnant magnetization of about 5000 Gauss, assuming a demagnetization force of about 1200 Oersted is applied. About 10,000 Gauss (i.e., 1 Tesla) is required to magnetize the Pt-23% wtCo material.

Figure 2:
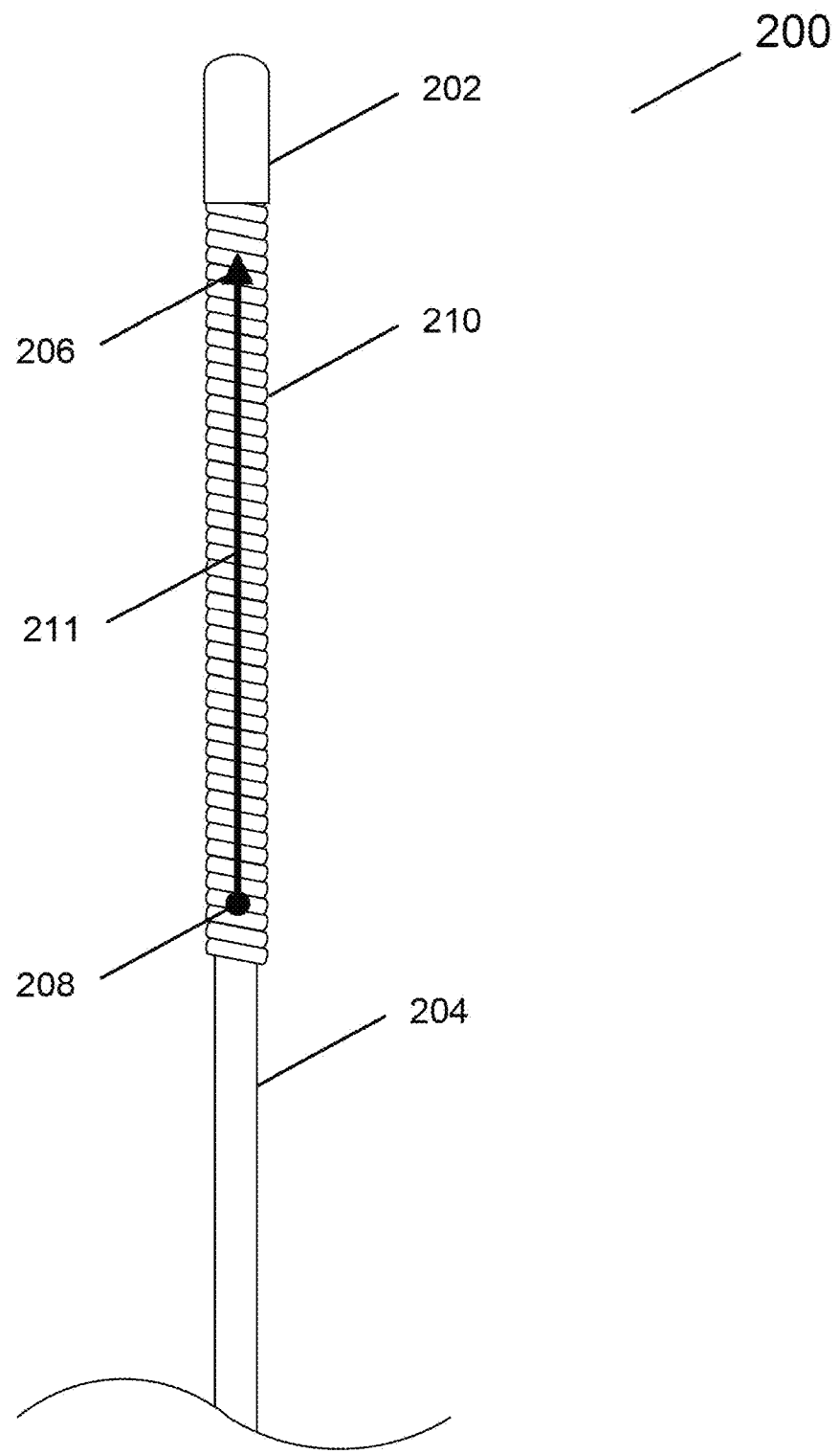
FIG. 2 is a schematic drawing of a magnetically controllable guidewire for interventional medical procedures possessing a single platinum cobalt alloy coil with the magnetization aligned with the vertical upward direction in accordance with one embodiment of the present invention.

FIG. 2 is a schematic drawing of a magnetically controllable medical device in the form of a guidewire 200. The guidewire 200 includes a single platinum cobalt alloy coil 210 with the permanent magnetization 211 (also called orientation) aligned with the vertical upward direction. The guidewire possesses a cap 202, which is connected to the coil 210. A supporting wire 204 is used, which may extend several meters in length. The supporting wire 204 is connected to the coil 210. The North magnetization 206 is at the top of the magnetization direction 211. The South magnetization 208 is at the bottom of the magnetization direction 211.

Figure 3:
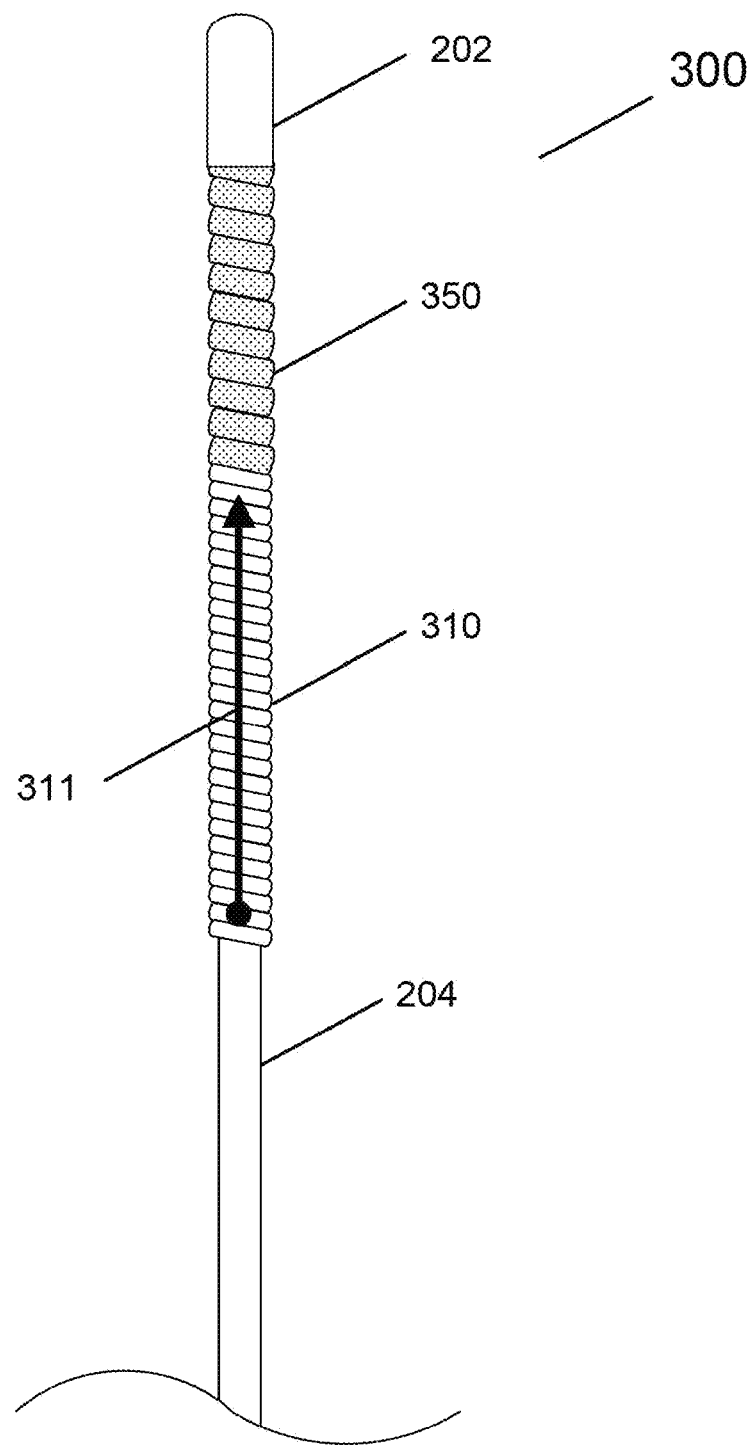
FIG. 3 is a schematic drawing of a magnetically controllable guidewire for interventional medical procedures possessing a single platinum cobalt alloy coil with the magnetization aligned with the vertical upward direction, which is proximally attached to a nonmagnetic coil in accordance with one embodiment of the present invention.

FIG. 3 is a schematic drawing of a magnetically controllable medical device in the form of a guidewire 300 possessing a single platinum cobalt alloy coil 310 with the permanent magnetization 311 aligned with the vertical upward direction, which is proximally attached to a nonmagnetic coil 350. The guidewire 300 possesses a cap 202, which is connected to the nonmagnetic coil 350. A supporting wire 204 is used, which may extend several meters in length. The supporting wire 204 is connected to the coil 310.

Figure 4:
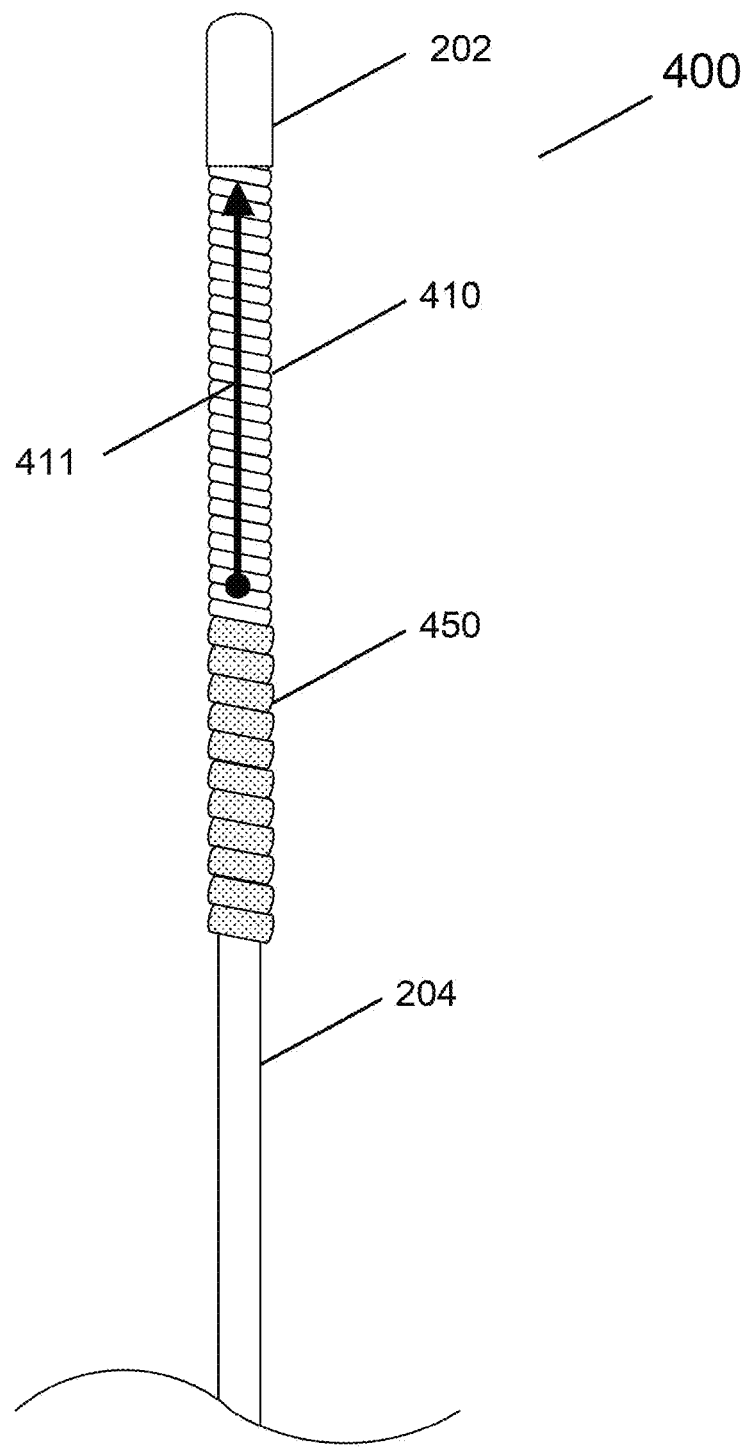
FIG. 4 is a schematic drawing of a magnetically controllable guidewire possessing a single platinum cobalt alloy coil with the magnetization aligned with the vertical upward direction, which is distally attached to a nonmagnetic coil in accordance with one embodiment of the present invention.

FIG. 4 is a schematic drawing of a magnetically controllable medical device in the form of a guidewire 400 possessing a single platinum cobalt alloy coil 410 with the permanent magnetization 411 aligned with the vertical upward direction, which is distally attached to a nonmagnetic coil 450. The guidewire possesses a cap 202, which is connected to the platinum cobalt alloy coil 410. A supporting wire 204 is used, which may extend several meters in length. The supporting wire 204 is connected to the nonmagnetic coil 450.

Figure 5:
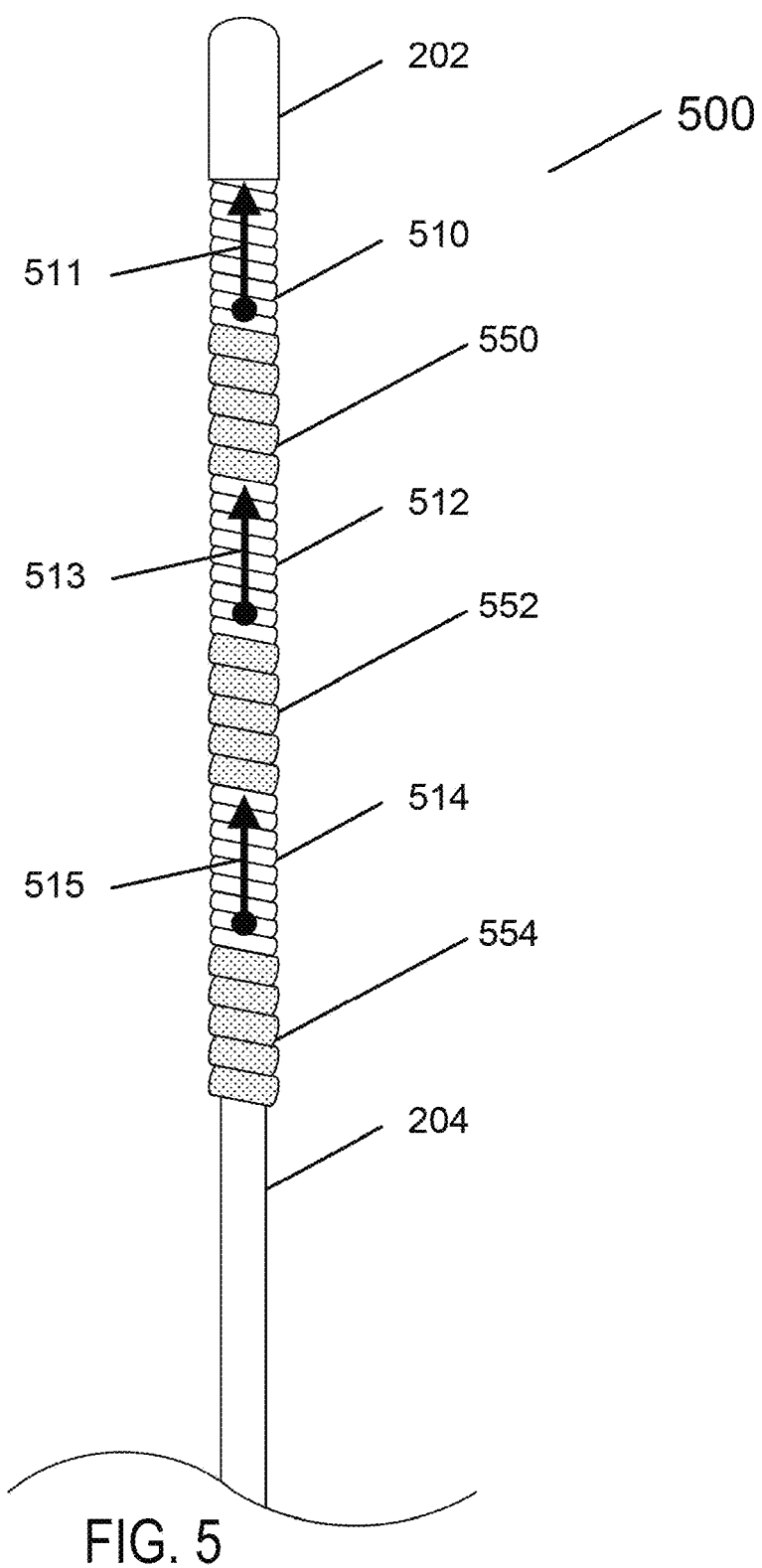
FIG. 5 is a schematic drawing of a magnetically controllable guidewire possessing three platinum cobalt alloy coils with all magnetizations aligned with the vertical upward direction, which are separated by three nonmagnetic coils in accordance with one embodiment of the present invention.

FIG. 5 is a schematic drawing of a magnetically controllable medical device in the form of a guidewire 500 including three platinum cobalt alloy coils 510, 512, and 514 with all permanent magnetizations 511, 513, and 515, respectively, aligned with the vertical upward direction, which are separated by three nonmagnetic coils 550, 552, and 554, respectively. The guidewire 500 possesses a cap 202, which is connected to one of the three platinum cobalt alloy coils 510. A supporting wire 204 is used, which may extend several meters in length. The supporting wire 204 is connected to the bottom nonmagnetic coil 554.

Figure 6:
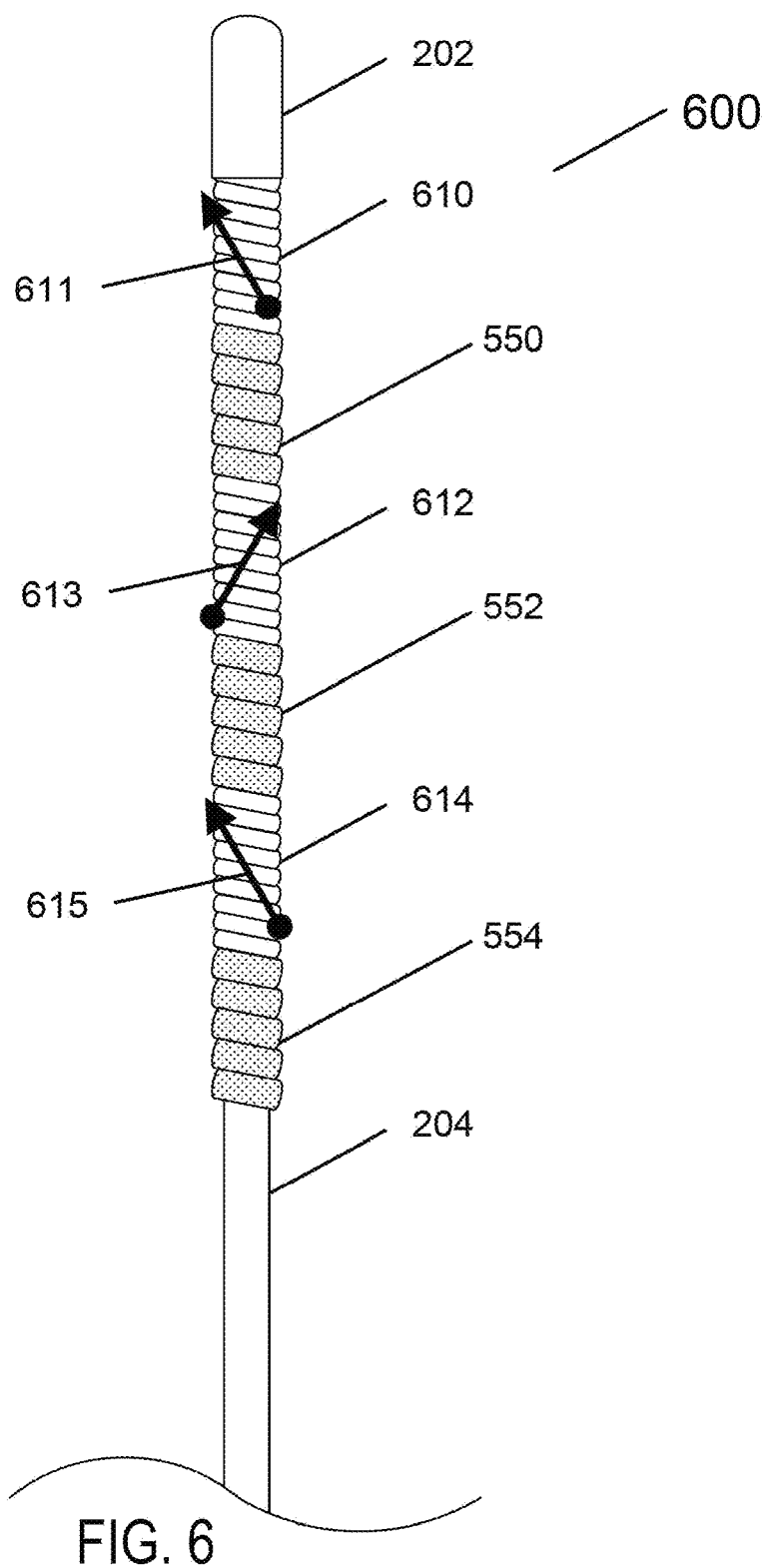
FIG. 6 is a schematic drawing of a magnetically controllable guidewire possessing three platinum cobalt alloy coils with all magnetizations offset from the vertical upward direction, which are separated by three nonmagnetic coils in accordance with one embodiment of the present invention.

FIG. 6 is a schematic drawing of a magnetically controllable medical device in the form of a guidewire 600 including three platinum cobalt alloy coils 610, 612, and 614, with all permanent magnetizations 611, 613, and 615, respectively, offset from the vertical upward direction, which are separated by three nonmagnetic coils 550, 552, and 554, respectively. The guidewire possesses a cap 202, which is connected to one of the three platinum cobalt alloy coils 610. A supporting wire 204 is used, which may extend several meters in length. The supporting wire 204 is connected to the bottom nonmagnetic coil 554.

Figure 7:
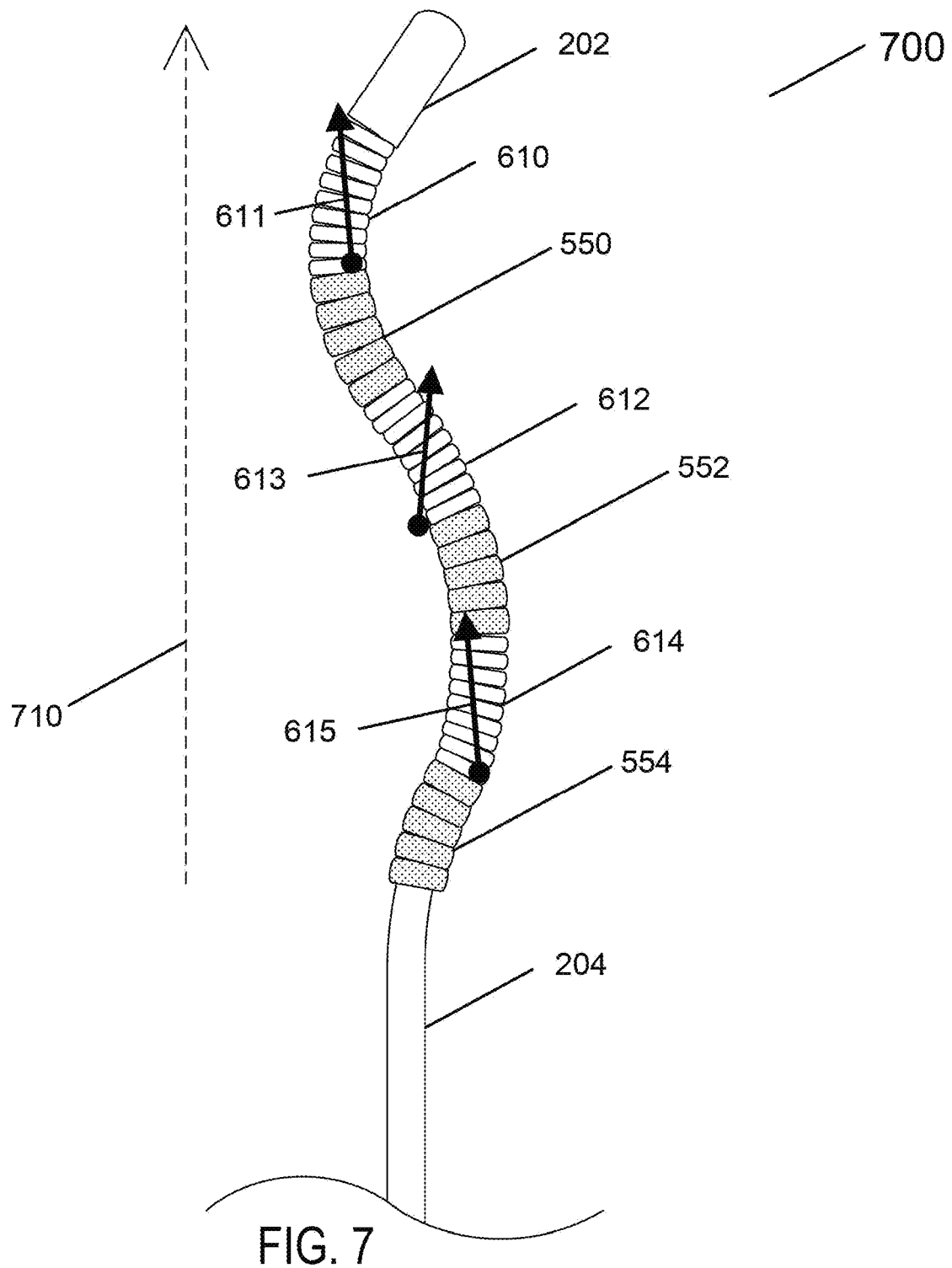
FIG. 7 is a schematic drawing of the magnetically controllable guidewire described in FIG. 6 illustrating a new shape of the device when the device subjected to an external magnetic field oriented in the vertical upward direction.

FIG. 7 is a schematic drawing of the guidewire described in FIG. 6 which forms a new shape (700) when subjected to an external magnetic field 710 oriented in the vertical upward direction. The external magnetic field 710 results in clockwise magnetic torques of the top 610 and bottom 614 platinum cobalt alloy coils, which are due to the magnetizations of the top 611 and bottom 615 platinum cobalt alloy coils attempting to align with the external magnetic field 710. Likewise, the middle platinum cobalt alloy coil 612 experiences a counterclockwise magnetic torque as its magnetization 613 attempts to align with the external magnetic field 710. As a result, a new guidewire shape 700 is made possible, as compared to that depicted in FIG. 6, by applying the vertically-orientated external magnetic field 710.

Figure 8:
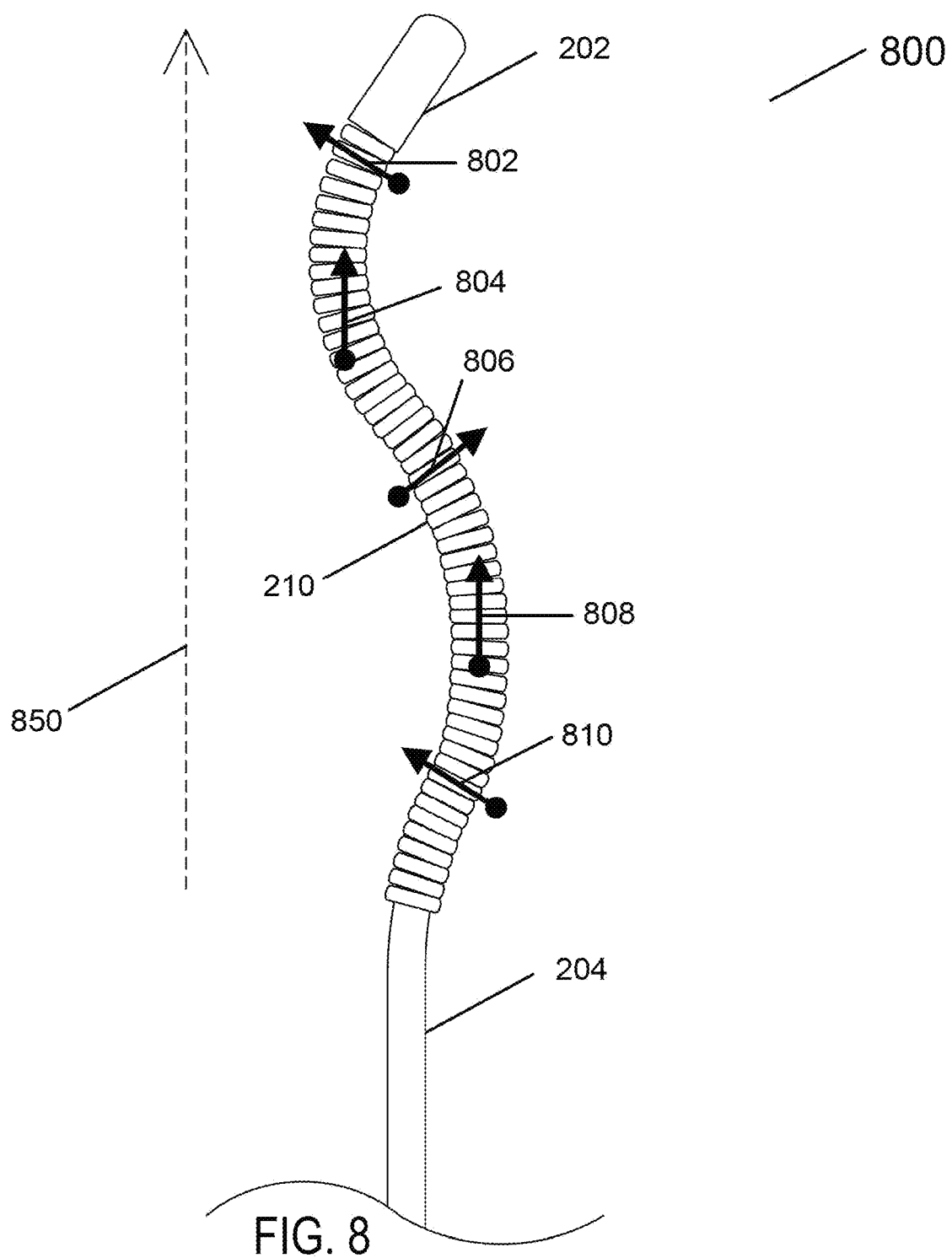
FIG. 8 is a schematic drawing of a magnetically controllable guidewire possessing a single platinum cobalt alloy coil with different magnetizations along its length which forms a new shape when subjected to an external magnetic field oriented in the vertical upward direction in accordance with one embodiment of the present invention.

FIG. 8 is a schematic drawing of a magnetically controllable medical device in the form of a guidewire 800 including a single platinum cobalt alloy coil 210 with different and distinct permanent magnetizations along its length 802, 804, 806, 808, and 810, which forms a new shape when subjected to an external magnetic field 850 oriented in the vertical upward direction. The guidewire possesses a cap 202, which is connected to the platinum cobalt alloy coil 210. A supporting wire 204 is used, which may extend several meters in length. The supporting wire 204 is connected to the bottom of the platinum cobalt alloy coil 210. The orientations of the magnetizations 802, 804, 806, 808, and 810, along the platinum cobalt coil are oriented so as to result in the depicted shape when an external magnetic field 850 is applied. The magnetizations at the top and bottom of the platinum cobalt coil, 802 and 810, respectively, experience a clockwise magnetic torque due to the external magnetic field 850. The magnetization near the middle of the platinum cobalt coil 806 experiences a counterclockwise magnetic torque due to the external magnetic field 850. The remaining two magnetization near the top and bottom of the platinum cobalt coil 804 and 808, respectively, are nearly aligned with the external magnetic field 850 and experience little magnetic torque. However, these magnetized regions will attempt to align with the external magnetic field 850 if the orientation of the guidewire 800 is perturbed.

Figure 9:
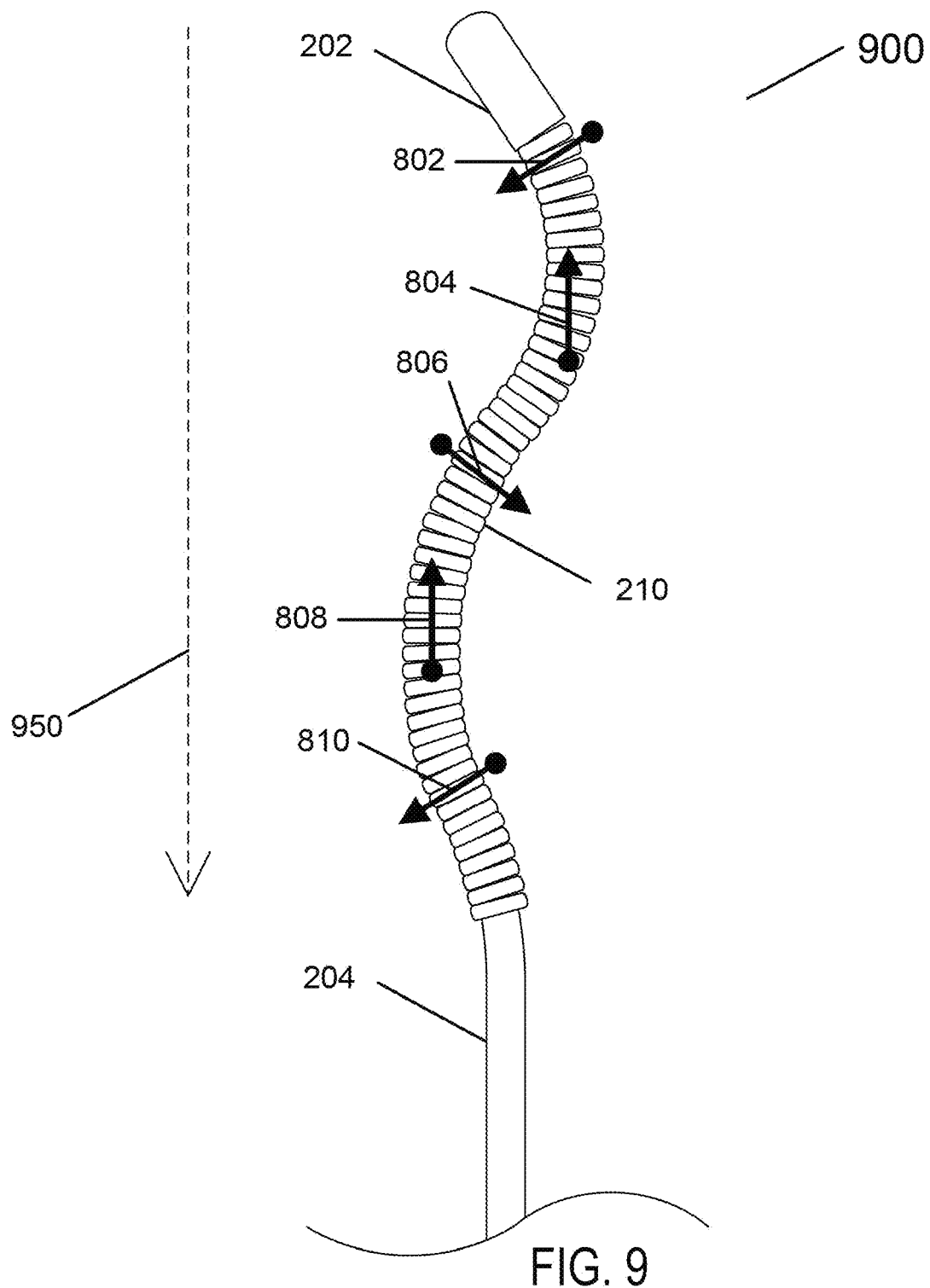
FIG. 9 is a schematic drawing of the guidewire described in FIG. 8 which forms a reversed shape when subjected to an external magnetic field oriented in the vertical downward direction.

FIG. 9 is a schematic drawing of the guidewire 800 described in FIG. 8 which forms the reversed shape 900 when subjected to an external magnetic 950 field oriented in the vertical downward direction. The orientations of the magnetizations along the platinum cobalt coil 802, 804, 806, 808, and 810 are oriented so as to result in the depicted shape when an external magnetic field 850 is applied. By reversing the external magnetic field 950 from that depicted in FIG. 8, the guidewire's shape is also reversed. The magnetizations at the top and bottom of the platinum cobalt coil 802 and 810, respectively, experience a counterclockwise magnetic torque due to the external magnetic field 950. The magnetization near the middle of the platinum cobalt coil 806 experiences a clockwise magnetic torque due to the external magnetic field 950. The remaining two magnetization near the top and bottom of the platinum cobalt coil are nearly aligned with the external magnetic field 950 and experience little magnetic torque. However, these magnetized regions will attempt to align with the external magnetic field 950 if the orientation of the guidewire 900 is perturbed. By alternating the external magnetic field 950 in time between that depicted in FIG. 8 and that depicted in FIG. 9, the guidewire can be made to vibrate or wiggle, thereby overcoming static friction against contacting surfaces and relieving tension along the supporting wire 204.

Figure 10:
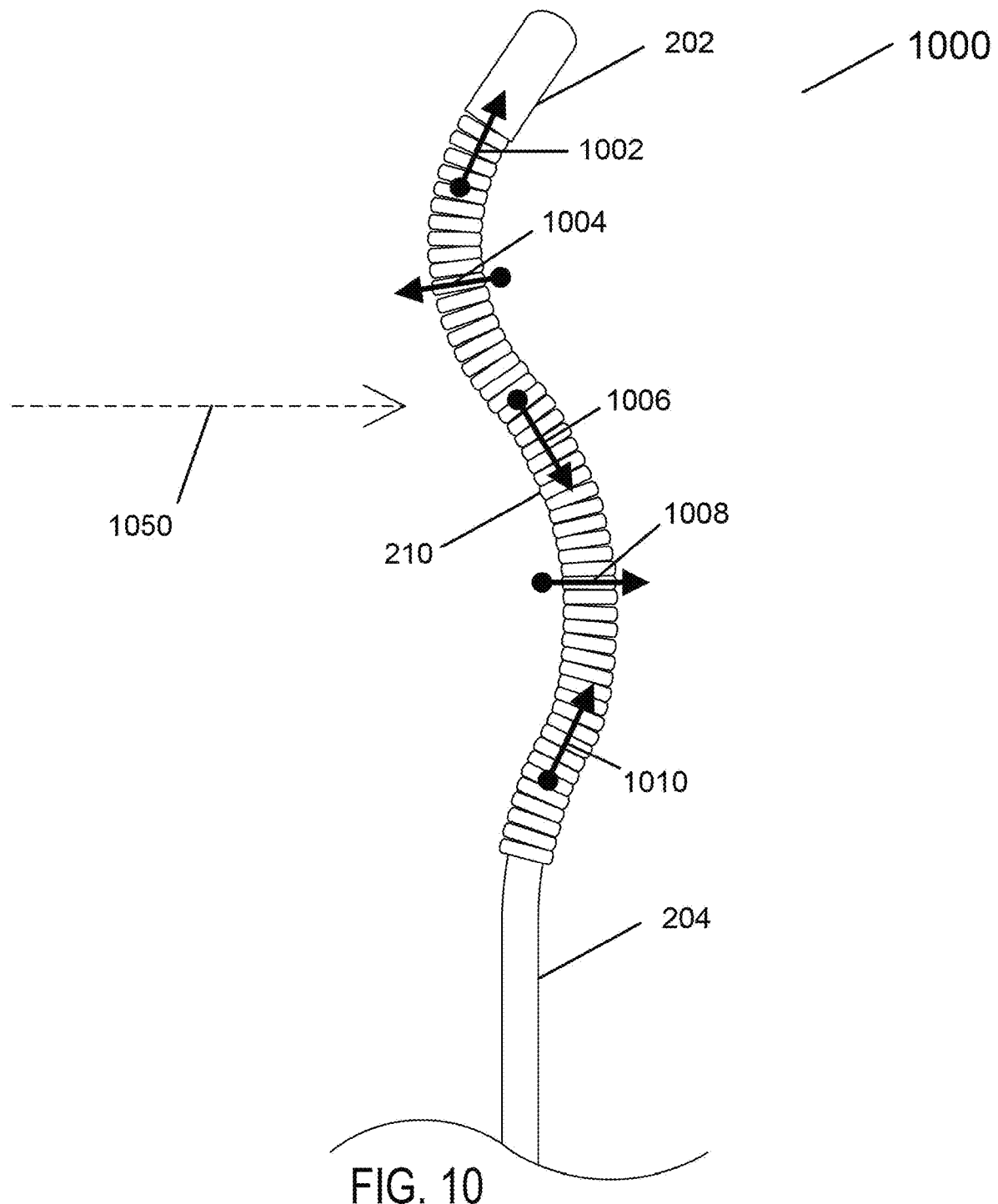
FIG. 10 is a schematic drawing of a magnetically controllable guidewire possessing a single platinum cobalt alloy coil with different magnetizations along its length which forms the same shape as that device depicted in FIG. 8 when subjected to an external magnetic field oriented in the horizontal rightward direction in accordance with one embodiment of the present invention.

FIG. 10 is a schematic drawing of a magnetically controllable medical device in the form of a guidewire 1000 including a single platinum cobalt alloy coil 210 with different magnetizations along its length (1002, 1004, 1006, 1008, and 1010) which forms the same shape as that depicted in FIG. 8 when subjected to an external magnetic field 1050 oriented in the horizontal rightward direction. The guidewire possesses a cap 202, which is connected to the platinum cobalt alloy coil 210. A supporting wire 204 is used, which may extend several meters in length. The supporting wire 204 is connected to the bottom of the platinum cobalt alloy coil 210. The orientations of the magnetizations along the platinum cobalt coil (1002, 1004, 1006, 1008, and 1010) are oriented so as to result in the depicted shape when an external magnetic field 1050 is applied. The magnetizations at the top and bottom of the platinum cobalt coil (1002 and 1010, respectively) experience a clockwise magnetic torque due to the external magnetic field 1050. The magnetization near the middle of the platinum cobalt coil (1006) experiences a counterclockwise magnetic torque due to the external magnetic field 1050. The remaining two magnetization near the top and bottom of the platinum cobalt coil (1004 and 1008, respectively) are nearly aligned with the external magnetic field 1050 and experience little magnetic torque. However, these magnetized regions will attempt to align with the external magnetic field 1050 if the orientation of the guidewire 1000 is perturbed. By alternating the external magnetic field 1050 so that the orientation of the external magnetic field 1050 is leftward pointing, the reverse guidewire shape of that depicted 1000 is accomplished (i.e., the left and right sides are reversed). By varying the external magnetic field 1050 in time, the guidewire can be made to vibrate or wiggle, thereby overcoming static friction against contacting surfaces and relieving tension along the supporting wire 204.

Figure 11A:
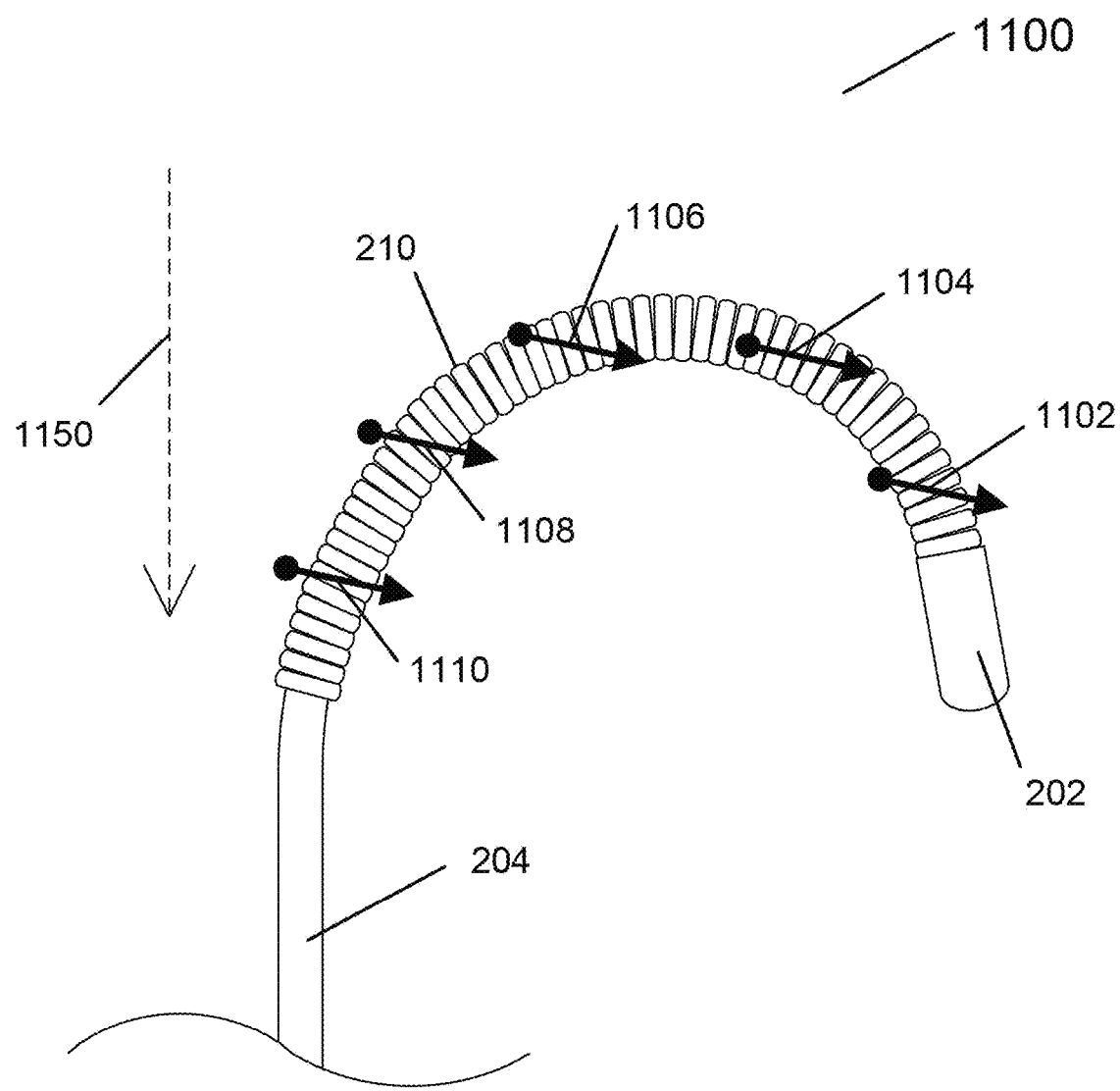
FIG. 11A is a schematic drawing of a magnetically controllable guidewire possessing a single platinum cobalt alloy coil with different magnetizations established along its length which are oriented to increase the ability to bend the guidewire in a clockwise direction when subjected to a vertical downward external magnetic field direction in accordance with one embodiment of the present invention.

FIG. 11A is a schematic drawing of a magnetically controllable medical device in the form of a guidewire 1100 including a single platinum cobalt alloy coil 210 with different magnetizations established along its length (1102, 1104, 1106, 1108, and 1110) which are oriented to increase the ability to bend the guidewire in a clockwise direction when subjected to a vertical downward external magnetic field direction 1150. The guidewire possesses a cap 202, which is connected to the platinum cobalt alloy coil 210. A supporting wire 204 is used, which may extend several meters in length. The supporting wire 204 is connected to the bottom of the platinum cobalt alloy coil 210. Mechanistically, the magnetizations (1102, 1104, 1106, 1108, and 1110) are oriented so that the magnetic torque on each corresponding region of the platinum cobalt coil 210 is maximized, thereby inducing the tightest possible bend.

Figure 11B:
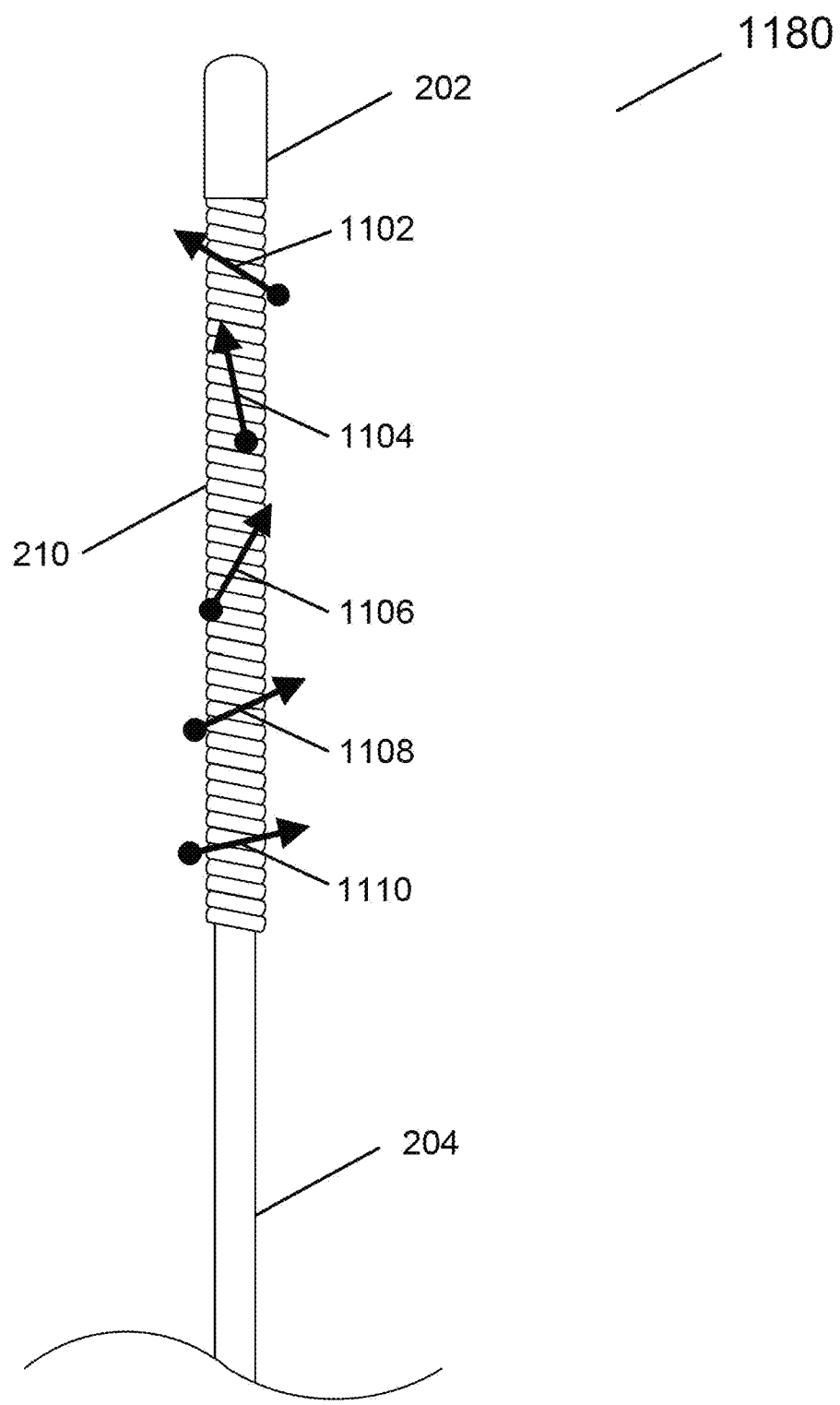
FIG. 11B is a schematic drawing of the guidewire of FIG. 11A in its vertically-aligned relaxed state which results when no external magnetic field is applied.

FIG. 11B is a schematic drawing of the guidewire 1100 of FIG. 11A in its vertically-aligned relaxed state 1180 which results when no external magnetic field is applied. As is shown, the magnetization orientations (1102, 1104, 1106, 1108, and 1110) continuously vary along the length of the platinum cobalt coil 210. While magnetically-motivated interaction forces and torques between neighboring regions of the platinum cobalt coil 210 may be generated which result in a perturbation of the guidewire's shape, it is possible to vary the stiffness of platinum cobalt coil 210 along its length to counteract these forces and torques so that the depicted shape results.

Figure 12A:
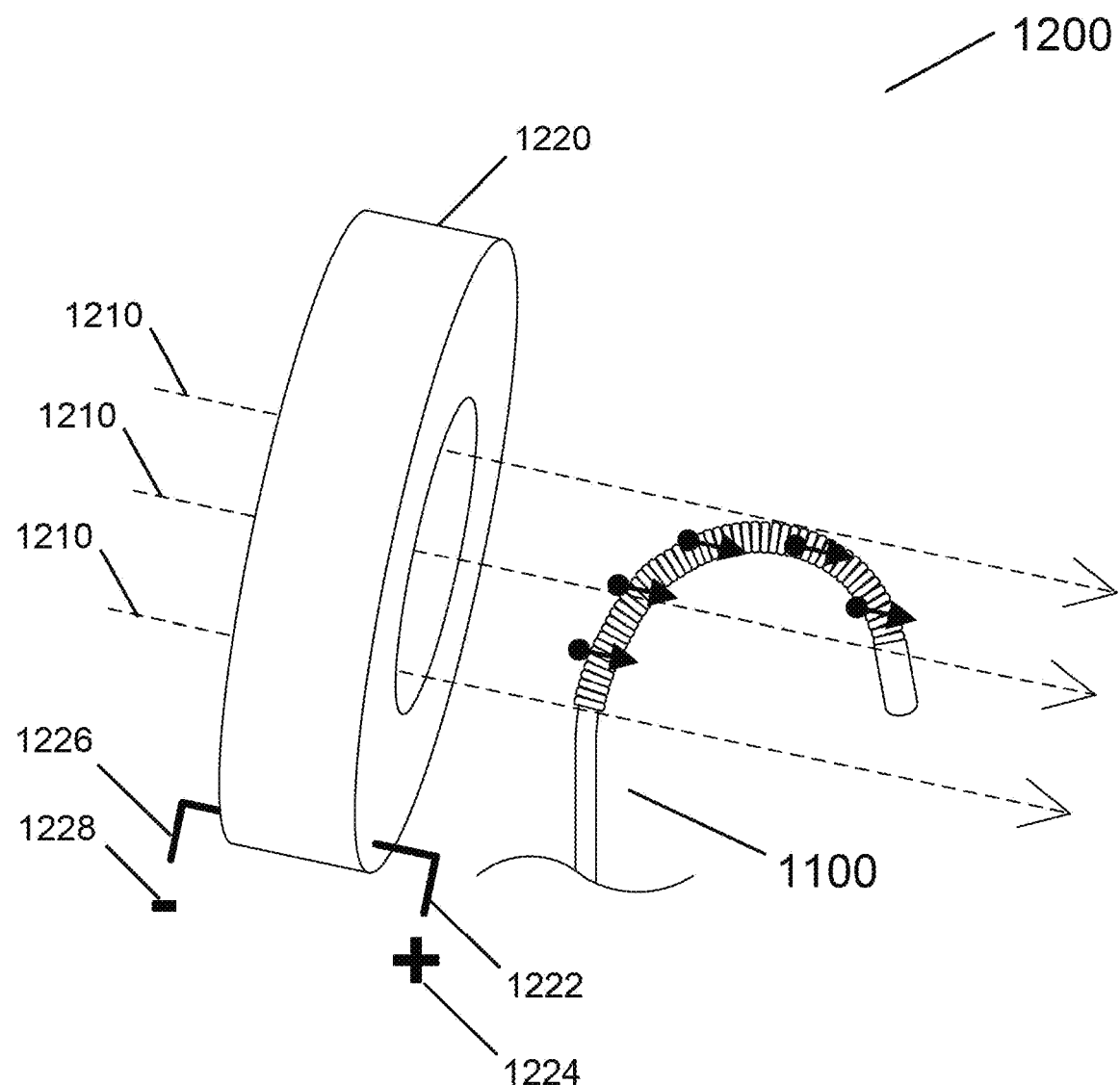
FIG. 12A is a schematic drawing of a magnetizer consisting of a single electromagnet which generates a relatively uniform magnetic field which results in the orientations depicted in the guidewire of FIG. 11A when positioned as shown for establishing permanent magnetization.

FIG. 12A is a schematic drawing of a magnetizer 1200 consisting of a single electromagnet 1220 which generates a relatively uniform magnetic field 1210 which results in the preferred magnetization orientations directions depicted in the guidewire of FIG. 11A 1100 when positioned as shown. This positioning may be within packaging and after sterilization as noted above. The electromagnet 1220 is powered by a positive lead wire 1222 and a negative lead wire 1226. The positive lead wire 1222 is noted by a plus ("+") symbol 1224. The negative lead wire 1226 is noted by a minus ("−") symbol 1228. As a direct current is fed into the electromagnetic coil 1220 from the positive lead wire 1222 to the negative lead wire 1226, windings within the electromagnetic coil 1220 circulate the current in a counterclockwise fashion around the electromagnetic coil's 1220 cylindrical axis (which generally points from left to right), resulting in a relatively uniform magnetic field 1210 which also generally points from left to right. This configuration of the electromagnetic coil 1220 and its associated magnetic field 1210 allows for the preferred magnetization orientations depicted in FIG. 11A 1100 to be established, which assumes that the guidewire 1100 is properly shaped and held with the preferred bend during the programing of the preferred magnetizations using the electromagnetic coil 1220. The packaging may be useful for the desired positioning of the guidewire 1100.

Figure 12B:
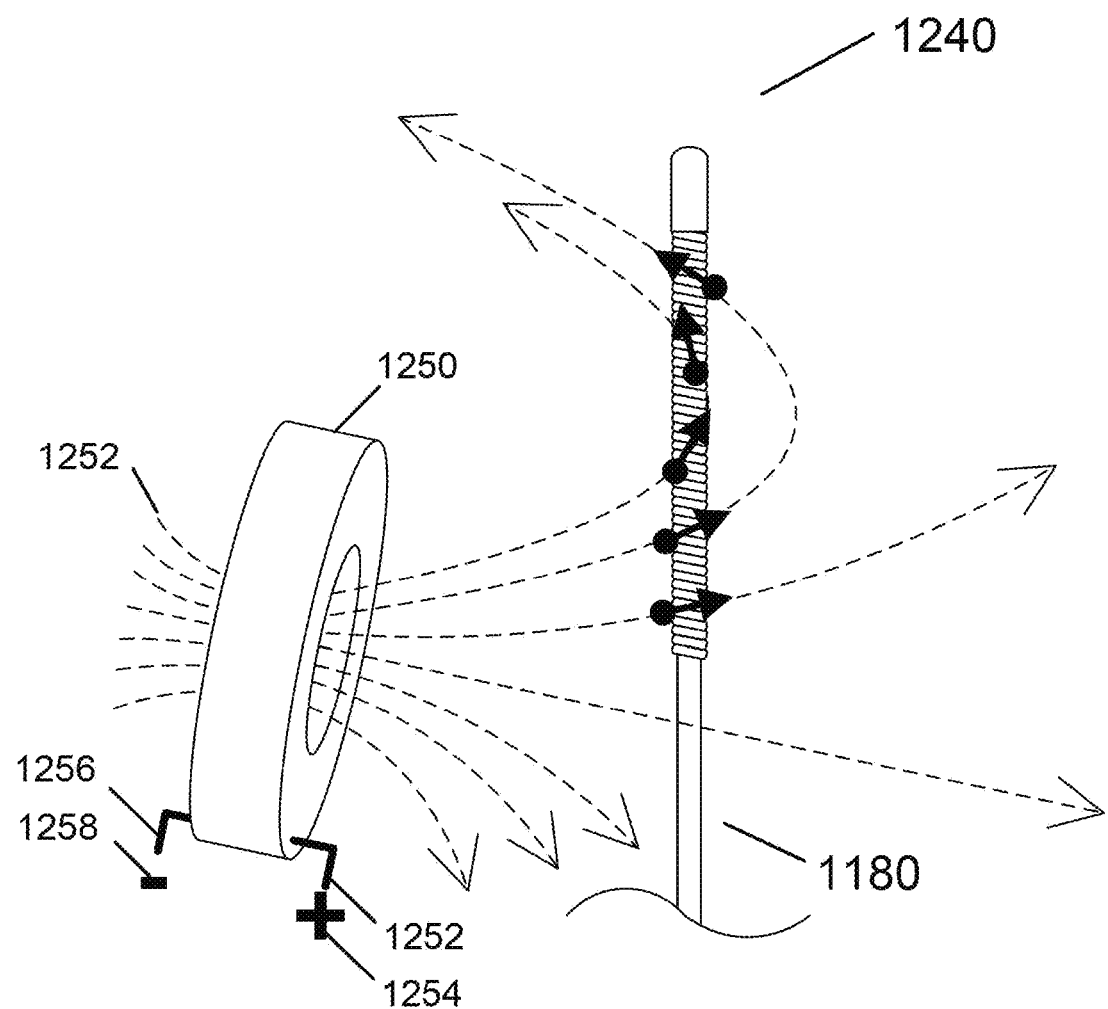
FIG. 12B is a schematic drawing of a magnetizer consisting of a single electromagnet which generates a nonuniform magnetic field which results in the preferred magnetizations directions depicted in the guidewire of FIG. 11B.

FIG. 12B is a schematic drawing of a magnetizer 1240 consisting of a single electromagnet 1250 which generates a non-uniform magnetic field 1252 which results in the preferred magnetizations directions depicted in the guidewire of FIG. 11B 1180. The electromagnet 1250 is powered by a positive lead wire 1252 and a negative lead wire 1256. The positive lead wire 1252 is noted by a plus ("+") symbol 1254. The negative lead wire 1256 is noted by a minus ("−") symbol 1258. As a direct current is fed into the electromagnetic coil 1250 from the positive lead wire 1252 to the negative lead wire 1256, windings within the electromagnetic coil 1250 circulate the current in a counterclockwise fashion around the electromagnetic coil's 1250 cylindrical axis (which generally points from left to right), resulting in a non-uniform magnetic field 1252 which also generally points from left to right within the bore of the electromagnetic 1250. This configuration of the electromagnetic coil 1250 and its associated non-uniform magnetic field 1252 allows for the preferred magnetization orientations depicted in FIG. 11B 1180 to be established, which assumes that the guidewire 1100 is properly held in the straight orientation during the programing of the preferred magnetizations using the electromagnetic coil 1250.

Figure 13:
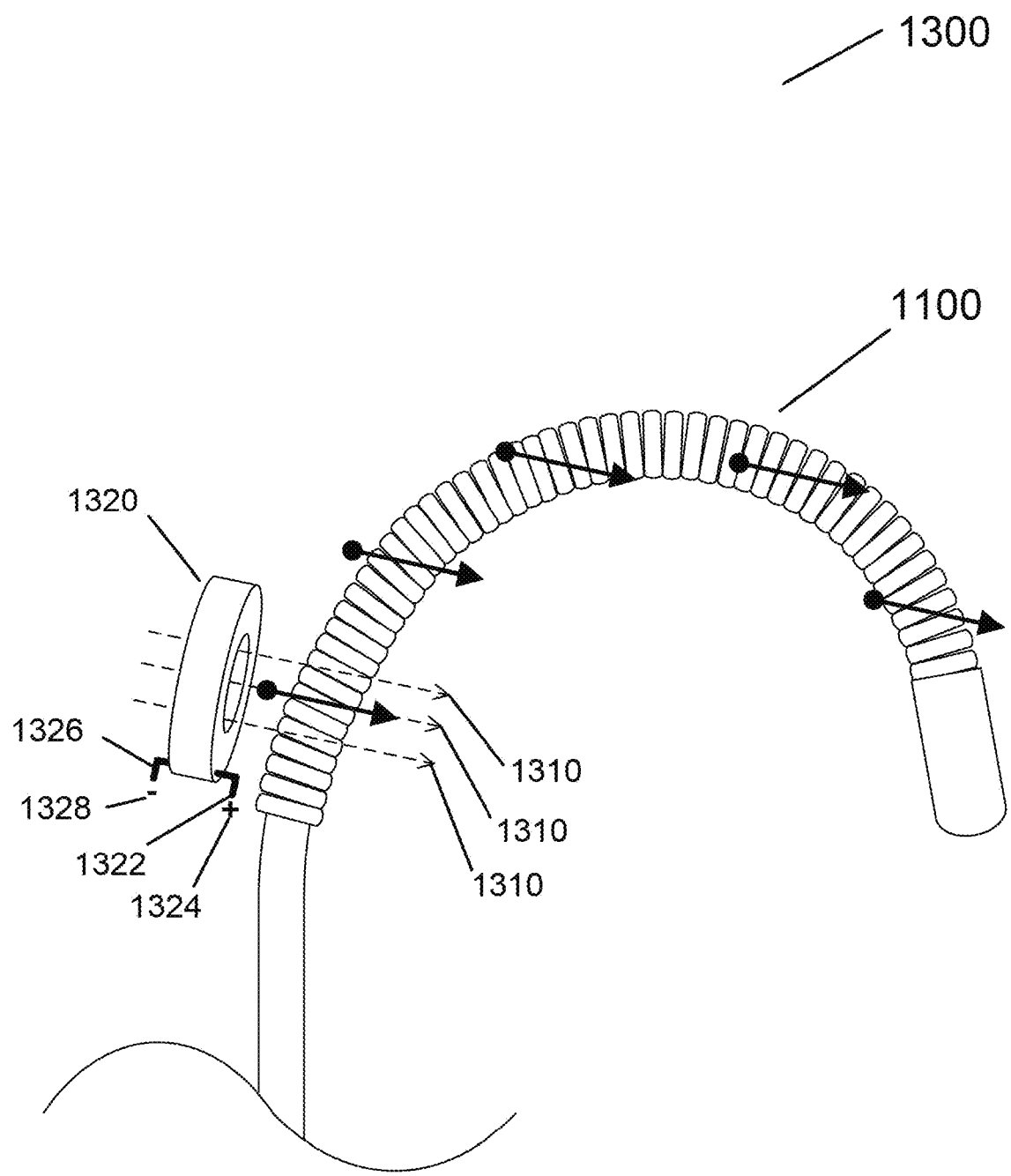
FIG. 13 is a schematic drawing of a magnetizer consisting of a single smaller electromagnet which generates a magnetic field over discrete regions of the platinum cobalt coil to achieve the magnetization orientations depicted in the guidewire of FIG. 11A when positioned as shown.

FIG. 13 is a schematic drawing of a magnetizer 1300 consisting of a single smaller electromagnet 1310 which generates a magnetic field 1310 over discrete regions of the platinum cobalt coil to achieve the magnetization orientations depicted in the guidewire of FIG. 11A. The electromagnet 1320 is powered by a positive lead wire 1322 and a negative lead wire 1326. The positive lead wire 1322 is noted by a plus ("+") symbol 1324. The negative lead wire 1326 is noted by a minus ("−") symbol 1328. As a direct current is fed into the electromagnetic coil 1320 from the positive lead wire 1322 to the negative lead wire 1326, windings within the electromagnetic coil 1320 circulate the current in a counterclockwise fashion around the electromagnetic coil's 1320 cylindrical axis (which generally points from left to right), resulting in a magnetic field 1310 which also generally points from left to right. This configuration of the electromagnetic coil 1320 and its associated magnetic field 1310 allows for the preferred magnetization orientations depicted in FIG. 11A 1100 to be established on a region-by-region basis, where the electromagnetic coil 1320 is used to separately induce the preferred magnetization orientations for each region along the platinum cobalt coil. It is envisioned that multiple magnetization coils similar to that depicted 1320 can be used together to more efficiently program the preferred magnetization along the guidewire depicted in FIG. 11A 1100.

Figures 14A, 14B:
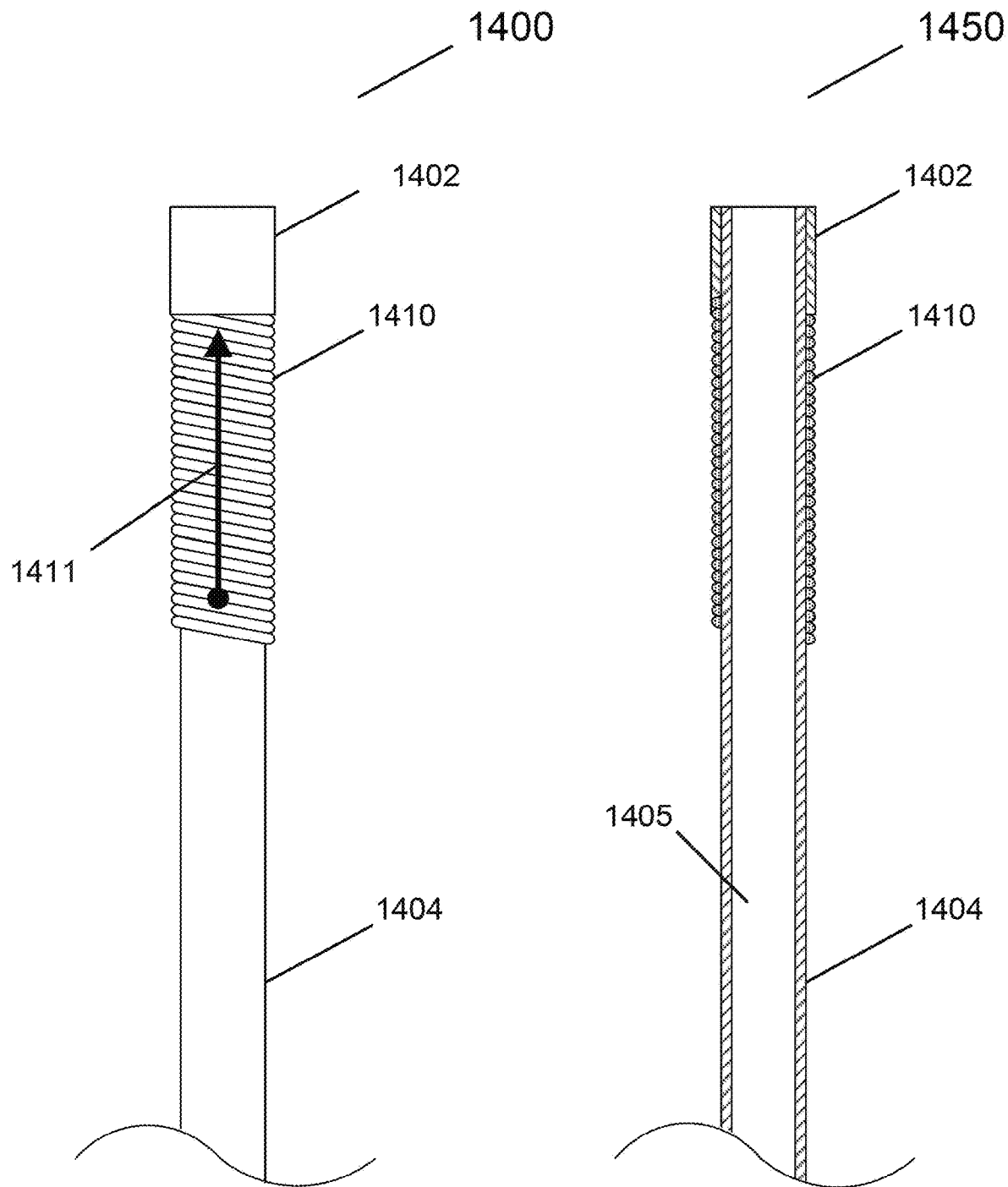
FIG. 14A is a schematic drawing of a magnetically controllable catheter possessing a platinum cobalt alloy coil with the magnetization aligned with the vertical upward direction in accordance with one embodiment of the present invention.
FIG. 14B is a schematic cross section view of the catheter depicted in FIG. 14A.

FIG. 14A is a schematic drawing of a magnetically controllable medical device in the form of a catheter 1400 possessing a platinum cobalt alloy coil 1410 with the magnetization 1411 aligned with the vertical upward direction. The catheter 1400 possesses a cap 1402, which is connected to the platinum cobalt alloy coil 1410. A supporting lumen 1404 is used, which may extend several meters in length. Applying an external magnetic field induced a torque on the platinum cobalt coil 1410 in the direction of the external magnetic field, thereby enabling preferred navigational control of the catheter.

FIG. 14B is a cross section view of the catheter 1400 depicted in FIG. 14A, showing the interior 1450. The catheter possesses a cap 1402, which is connected to the platinum cobalt alloy coil 1410. A supporting lumen 1404 is used, which may extend several meters in length. Applying an external magnetic field induced a torque on the platinum cobalt coil 1410 in the direction of the external magnetic field, thereby enabling preferred navigational control of the catheter. The supporting lumen 1404 extends to the cap 1402 and maintains an open lumen 1405 for the passage of tools, therapies, interventions, and agents.

Figure 15:
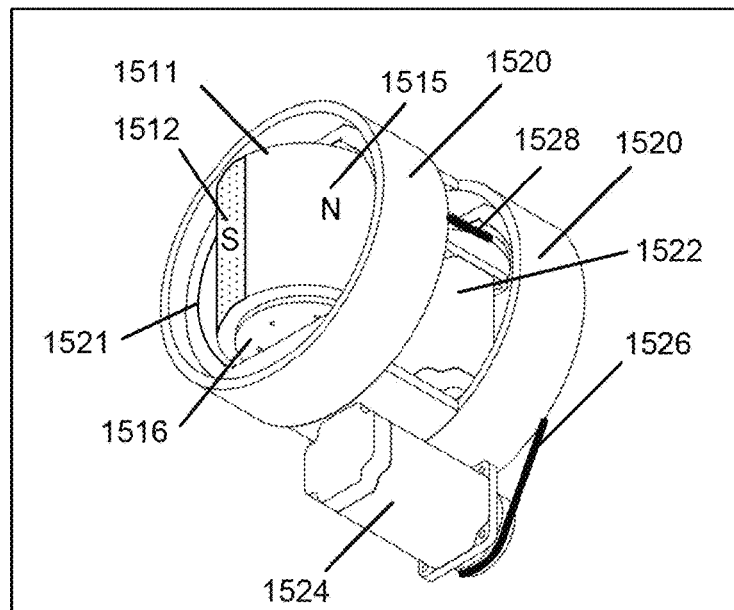
FIG. 15 is a schematic representation of an external magnet system for generating a magnetic field and gradient to magnetically control the programmable magnetic medical devices for interventional medical procedures in accordance with the present invention.
Figure 15:
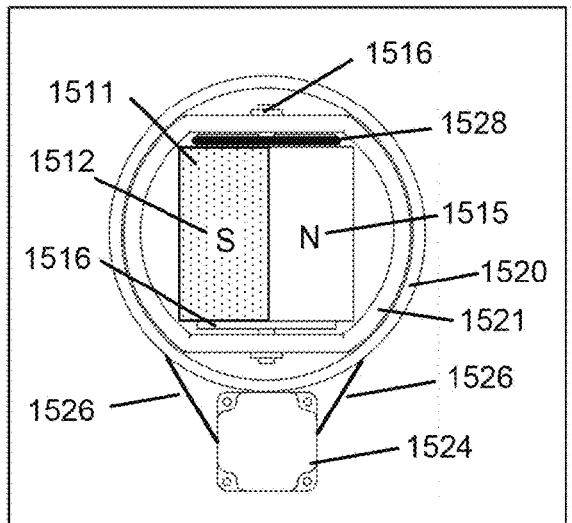
Figure 15:
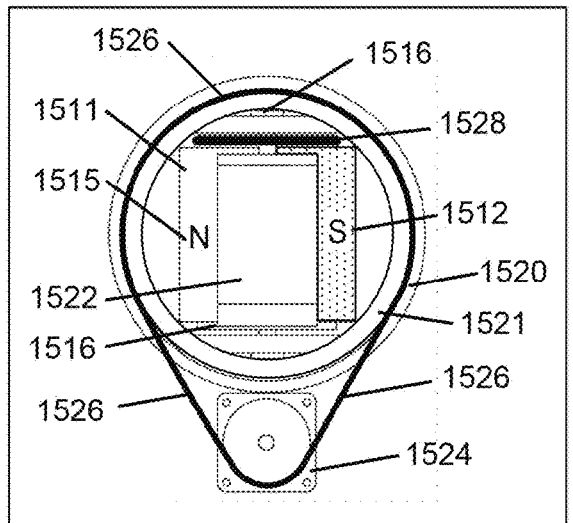

FIG. 15 is a drawing of an example external magnet system for generating a magnetic field and gradient to magnetically control the programmable magnetic devices. Subfigure 1502 depicts the isometric view of the example external magnet system. Subfigure 1504 depicts the front view of the example external magnet system. Subfigure 1506 depicts the rear view of the example external magnet system. The permanent magnet subassembly 1511 possesses a North and South magnetic pole (1514 and 1512, respectively). The sides of the permanent magnet subassembly 1511 are connected to endplates 1516 which are free to spin within the inner yoke assembly 1521 so that the permanent magnet subassembly 1511 can rotate in a manner that the North 1514 and South 1512 magnet poles switch positions. To accomplish this, the magnet drive motor 1522 with the magnet drive belt 1528 attached to one of the endplates 1516 is used. The inner yoke assembly 1521 is allowed to rotate within the outer support frame 1520. To accomplish this, the inner yoke drive motor 1524 with the inner yoke drive belt 1526 attached to the inner yoke assembly 1521 is used. In this configuration, the inner yoke drive motor 1524 turns the inner yoke drive belt 1526 which imparts rotation on the inner yoke assembly 1521. The magnet drive motor 1522 turns the magnet drive belt 1528 so as to spin the permanent magnet subassembly 1511. As a result, the permanent magnet subassembly 1511 can achieve any orientation in space, thereby creating the preferred external magnetic field orientations and corresponding temporal behavior.

This invention describes new methods and devices relating to the control and design of magnetically-controlled programmable magnetic devices. Current efforts to navigate tools within the body rely on transmitting forces and torques from the proximal end to the distal end of the tool, which can be several meters away. To enable control, devices must possess enough stiffness between proximal and distal ends so that forces and torques are reliably transmitted, without which control would be problematic. For this reason, current interventional devices are limited in how small and how flexible they can be manufactured. Use of an external magnetic field to apply forces and torques directly on the magnetic tip of interventional devices can overcome some of the limitations associated with manual device control. However, prior efforts to control magnetic-tipped devices using an external magnetic field have relied on high energy-product permanent magnets in the construction of the device's magnetic tip. Because the permanent magnets previously employed possess ceramic-like qualities, making them brittle and stiff, the manufacturing of ductile magnetic coils, wires, and braids has not been possible and efforts to make magnet-tipped guidewires smaller than 0.014 inches have not been commercially realized. Furthermore, because of demagnetization during the manufacturing process of small permanent magnets, large external magnetic field-generating systems are required. By leveraging a unique ductile magnetic alloy whose magnetization orientation can be programmed post manufacturing of the final device, the disclosed invention overcomes prior limitations which have restricted the ability to make and control very small magnetic devices using a compact external magnetic field-generating system. As noted above platinum cobalt (PtCo) in the devices of the invention may be formed of wires less than 1 mm in diameter.

Further the medical devices of the invention may be formed as guidewire having an outer diameter less than 0.035 in, preferably equal to even less than 0.014 in. Further the medical devices of the invention may be formed as catheter with an outer diameter less than 2 mm and an inner diameter less than 1.5 mm. The advantages of the present invention are not limited to these smaller sizes and the devices of the present invention yield significant control advantages at more conventional larger sizes, but the present invention opens up a new class of magnetically controlled micro guidewires and micro catheters and micro-medical devices in general.

Figure 16:
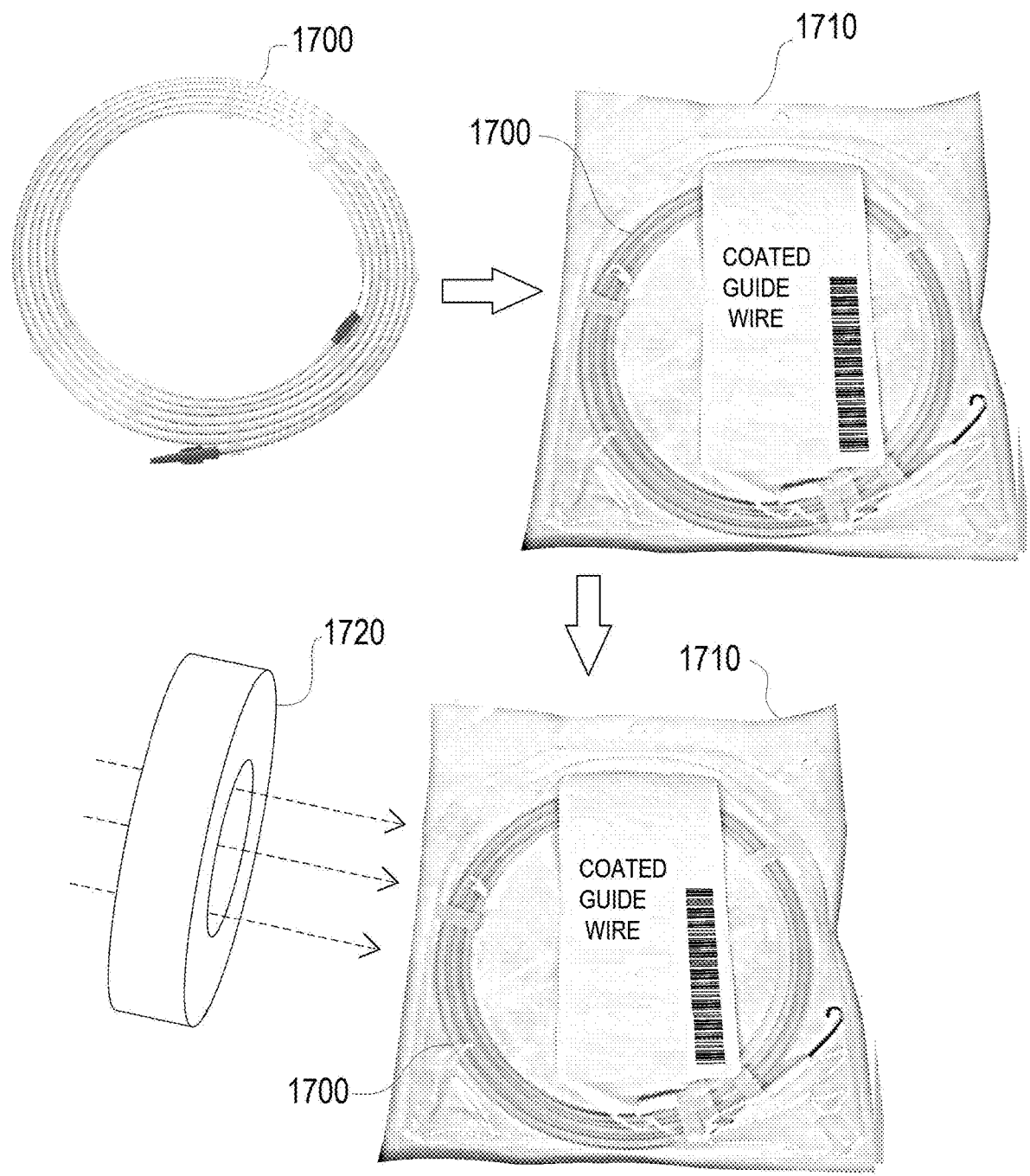
FIG. 16 schematically shows the formation of the programmable magnetic medical devices for interventional medical procedures in accordance with the present invention.

FIG. 16 schematically shows the formation of the programmable magnetic medical devices for interventional medical procedures in accordance with the present invention. Specifically the process begins with manufacturing a medical device 1700 for interventional medical procedures having magnetic materials which are without permanent magnetization. The device 1700 shown may be any of the guidewires shown and/or described above. The next step is packaging, in package 1710, and sterilizing the medical device. The final step is the establishing permanent magnetization within the magnetic materials of the device 1700 subsequent to manufacturing packaging and sterilization with a magnetizer 1720, wherein the permanent magnetization allows the medical device to be magnetically controllable. As shown the packaging 1710 may serve to properly position and hold the magnetic material in a proper position for programming the device 1700. While the invention has been shown in several particular embodiments it should be clear that various modifications may be made to the present invention without departing from the spirit and scope thereof. The scope of the present invention is defined by the appended claims and equivalents thereto.

What is claimed is:

1. A method of making magnetically controllable devices for interventional medical procedures comprising the steps of:

manufacturing a medical device for interventional medical procedures having magnetic materials which are without permanent magnetization, wherein the medical device is one of a wire, guidewire, catheter, radiofrequency wire, micro-catheter, braid, coil, lumen, thrombectomy system, stent, aspiration tool, drug-delivery tool, aneurysm-filling coil, electrical lead, and embolization system; and establishing permanent magnetization within the magnetic materials subsequent to manufacturing, wherein the permanent magnetization allows the medical device to be magnetically controllable;

wherein establishing permanent magnetization comprises using a magnet array to magnetize individual segments of the medical device; and wherein the individual segments have different magnetic orientations, strengths, and magnetization angles.

2. The method of making magnetically controllable devices for interventional medical procedures according to claim 1 further including the step of packaging the medical device for interventional medical procedures and wherein the step of establishing permanent magnetization occurs after packaging the medical device.

3. The method of making magnetically controllable devices for interventional medical procedures according to claim 2 further including the step of sterilizing the medical device for interventional medical procedures and wherein the step of establishing permanent magnetization occurs after sterilizing the medical device.

4. The method of making magnetically controllable devices for interventional medical procedures according to claim 1 wherein the magnetic material includes one of a platinum alloy or a palladium alloy.

5. The method of making magnetically controllable devices for interventional medical procedures according to claim 4 wherein the magnetic material includes one of platinum cobalt (PtCo), platinum iron (PtFe), cobalt palladium (CoPd), nickel platinum (NiPt), nickel palladium (NiPd), and alloys containing iron, platinum, and niobium.

6. The method of making magnetically controllable devices for interventional medical procedures according to claim 4 wherein the magnetic material includes platinum cobalt (PtCo).

7. The method of making magnetically controllable devices for interventional medical procedures according to claim 6 wherein the magnetic material includes platinum cobalt (PtCo) formed of wires less than 1 mm in diameter.

8. The method of making magnetically controllable devices for interventional medical procedures according to claim 4 wherein the medical device is one of a guidewire or a catheter.

9. The method of making magnetically controllable devices for interventional medical procedures according to claim 4 wherein the medical device is one of a guidewire having an outer diameter less than 0.035 in or a catheter with an outer diameter less than 2 mm.

* * * * *